United States Patent
Kawana et al.

(10) Patent No.: US 8,703,840 B2
(45) Date of Patent: Apr. 22, 2014

(54) DENTAL ADHESIVE MATERIAL KIT

(75) Inventors: Michiya Kawana, Kurashiki (JP); Hidemi Nakayama, Kurashiki (JP); Mitsuru Takei, Kurashiki (JP); Kenji Suzuki, Kurashiki (JP); Ai Hinamoto, Kurashiki (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 218 days.

(21) Appl. No.: 13/500,656

(22) PCT Filed: Mar. 25, 2011

(86) PCT No.: PCT/JP2011/001788
§ 371 (c)(1),
(2), (4) Date: Apr. 6, 2012

(87) PCT Pub. No.: WO2011/121965
PCT Pub. Date: Oct. 6, 2011

(65) Prior Publication Data
US 2012/0202913 A1 Aug. 9, 2012

(30) Foreign Application Priority Data
Mar. 30, 2010 (JP) .................................. 2010-079383

(51) Int. Cl.
*A61K 6/083* (2006.01)
*A61K 6/08* (2006.01)
*A61L 24/06* (2006.01)

(52) U.S. Cl.
USPC ............. 523/118; 523/116; 523/120; 522/60; 522/65; 522/81; 522/83; 522/84; 522/113; 522/120; 522/153; 522/178; 522/182; 522/908

(58) Field of Classification Search
CPC ... A61K 6/0023; A61K 6/0038; A61K 6/005; A61K 6/0052
USPC ............. 523/118, 116, 84, 60, 65, 71, 74, 81, 523/83, 908, 113, 120, 121, 183, 153, 178, 523/182
See application file for complete search history.

(56) References Cited

U.S. PATENT DOCUMENTS

| | | | | |
|---|---|---|---|---|
| 4,499,251 A | * | 2/1985 | Omura et al. | 526/278 |
| 4,540,722 A | * | 9/1985 | Bunker | 523/109 |
| 4,923,400 A | * | 5/1990 | Suzuki et al. | 433/226 |
| 5,908,879 A | | 6/1999 | Kawashima et al. | |
| 6,214,101 B1 | * | 4/2001 | Nakaseko | 106/35 |
| 7,963,769 B2 | * | 6/2011 | Qian | 433/228.1 |
| 8,545,225 B2 | * | 10/2013 | Takei et al. | 433/228.1 |
| 2008/0081889 A1 | | 4/2008 | Kawashima et al. | 526/181 |
| 2009/0048364 A1 | * | 2/2009 | Liu | 522/48 |
| 2009/0093563 A1 | * | 4/2009 | Qian | 522/79 |
| 2010/0087613 A1 | * | 4/2010 | Takei et al. | 526/313 |
| 2010/0130682 A1 | | 5/2010 | Hinamoto et al. | |
| 2010/0240798 A1 | * | 9/2010 | Kawashima et al. | 523/118 |
| 2011/0250557 A1 | * | 10/2011 | Qian | 433/9 |
| 2012/0115106 A1 | * | 5/2012 | Qian et al. | 433/203.1 |
| 2012/0115978 A1 | * | 5/2012 | Qian et al. | 522/175 |

FOREIGN PATENT DOCUMENTS

| | | | |
|---|---|---|---|
| JP | 53 110637 | | 9/1978 |
| JP | 2 258602 | | 10/1990 |
| JP | 9 157124 | | 6/1997 |
| JP | 10 36116 | | 2/1998 |
| JP | 2010235458 A | * | 10/2010 |
| WO | 2006 016545 | | 2/2006 |
| WO | 2008 087977 | | 7/2008 |

OTHER PUBLICATIONS

International Search Report Issued Jun. 28, 2011 in PCT/JP11/01788 Filed Mar. 25, 2011.

* cited by examiner

*Primary Examiner* — Sanza McClendon
(74) *Attorney, Agent, or Firm* — Oblon, Spivak, McClelland, Maier & Neustadt, L.L.P.

(57) ABSTRACT

The present invention provides a dental adhesive material kit having excellent bond durability. The present invention is represented by a dental adhesive material kit containing a dental aqueous adhesive composition (A) and a multi-part type dental nonaqueous curable composition (B). The dental aqueous adhesive composition (A) contains a polymerizable monomer (a) having an acidic group, an aliphatic polymerizable monomer (b) having no acidic group, water (c), and an amine-based reducing agent (d1) containing no sulfur atom. The multi-part type dental nonaqueous curable composition (B) contains an aliphatic polymerizable monomer (b) having no acidic group, an aromatic polymerizable monomer (e) having no acidic group, a powdery water-soluble reducing compound (f) containing a sulfur atom, an organic peroxide (g), and an amine-based reducing agent (d2) containing no sulfur atom.

11 Claims, No Drawings

DENTAL ADHESIVE MATERIAL KIT

TECHNICAL FIELD

The present invention relates to a dental adhesive material kit. Specifically, the present invention relates to a dental adhesive material kit that combines an aqueous adhesive composition and a nonaqueous curable composition, and that exhibits high bond durability to an adherend containing water.

BACKGROUND ART

Adhesive materials have been used for the restorative care of wet bodies such as biological hard tissues like teeth and bones. As such an adhesive material to be used for wet bodies, a resin-based curable composition containing a radical polymerizable monomer, a polymerization initiator, etc., has been widely used.

Proposals that have been conventionally made to enhance the adhesive properties of the resin-based curable composition to a wet body, particularly to biological hard tissues, can be roughly classified into two types. Those are: a proposal about a radical polymerizable monomer having an acidic group intended to enhance the chemical/physical interaction with a substrate as a bonding target such as teeth and bones, and a proposal about a polymerization initiator intended to allow efficient polymerization and curing of the curable composition that contains a radical polymerizable monomer having an acidic group on biological hard tissues.

As a dental adhesive agent using such a resin-based curable composition, so-called self-etching-type adhesive agents have been widely used in recent years. In such a self-etching-type adhesive agent, a self-etching primer that contains a polymerizable monomer having an acidic group and a hydrophilic polymerizable monomer is first applied to the surface of tooth structure, and then a bonding material is applied thereon. Lately, a photocurable one-component dental adhesive agent having both functions as a self-etching primer and as a bonding material in combination has been put to practical use.

In order for such a dental adhesive agent to exhibit sufficient adhesiveness to tooth structure, particularly to dentin, it is necessary to have an decalcifying effect to allow an acidic component to dissolve the surface of dentin, a penetration effect to allow a polymerizable monomer component to penetrate into collagen of dentin, and a curing effect to allow the polymerizable monomer component that has penetrated therein to solidify to form a hybrid layer with the collagen.

When a resin-based curable composition is bonded to a wet body, it is often that, among the above-mentioned decalcifying effect, penetration effect, and curing effect, the curing effect is reduced because of curing inhibition due to oxygen present at the bonding interface, resulting in a failure to obtain sufficient bond strength. The curing inhibition of this type occurs remarkably, particularly when the curable composition is bonded to tooth dentin and bones that contain a large amount of oxygen.

Therefore, in order to suppress the curing inhibition due to oxygen contained in a wet body and to accelerate the polymerization curing reaction, a use of a redox polymerization initiator composed of a catalyst (oxidizing agent) and an accelerator (reducing agent) has been proposed.

Owing to significant development in curing light units, photocurable one-component dental adhesive agents have become widely used in dental clinics in recent years. However, such photocurable one-component dental adhesive agents cannot be used for restoration sites that are located out of the reach of light from a light irradiator, such as the lower bottom part of the inner part of a root canal, and the inner side of a restorative material.

On the other hand, in a dual cure-type curable composition using a redox polymerization initiator composed of an oxidizing agent and a reducing agent, the sites that are located out of the reach of light are cured by the redox polymerization initiator, and the sites that are located within the reach of light are cured in a short time by a photopolymerization initiator for which the polymerization curing time can be adjusted easily. The dual cure-type composition is used as a material for core construction when restoring a root canal part whose root canal has been formed by removing the tooth pulp of the root part in the case of very advanced dental caries.

The applicants have proposed a redox-curing type composition that contains a radical polymerizable monomer, and an oxidizing agent and a reducing agent of a redox polymerization initiator. In the redox-curing type composition, a water-soluble reducing agent is powder dispersed so that the curing reaction at the bonding interface is accelerated due to water in a wet body. For example, Patent Literature 1 proposes a redox curing-type nonaqueous curable composition that contains a liquid radical polymerizable monomer, an organic peroxide, and a powdery water-soluble reducing compound. The powdery water-soluble reducing compound is dispersed in the liquid radical polymerizable monomer to form the redox curing-type nonaqueous curable composition.

The redox curing-type nonaqueous curable composition according to Patent Literature 1 exhibits high adhesive properties also in the case of performing a pretreatment with a self-etching primer that has a high decalcifying effect and penetration effect before applying the composition to the surface of a tooth (Example 3, Patent Literature 1).

CITATION LIST

Patent Literature

Patent Literature 1: WO 2006/016545 A1

SUMMARY OF INVENTION

Technical Problem

However, the studies by the inventors have revealed that the bond durability of the above-mentioned redox curing-type nonaqueous curable composition of Patent Literature 1 leaves room for improvement.

Therefore, it is an object of the present invention to provide a dental adhesive material kit having excellent bond durability.

Solution to Problem

The present invention that has achieved the above-mentioned object is a dental adhesive material kit including a dental aqueous adhesive composition (A) and a multi-part type dental nonaqueous curable composition (B). In the dental adhesive material kit, the dental aqueous adhesive composition (A) contains a polymerizable monomer (a) having an acidic group, an aliphatic polymerizable monomer (b) having no acidic group, water (c), and an amine-based reducing agent (d1) containing no sulfur atom, and the multi-part type dental nonaqueous curable composition (B) contains an aliphatic polymerizable monomer (b) having no acidic group, an aromatic polymerizable monomer (e) having no acidic group, a powdery water-soluble reducing compound (f) containing a sulfur atom, an organic peroxide (g), and an amine-based reducing agent (d2) containing no sulfur atom.

In the dental adhesive material kit of the present invention, it is preferable that: the content of the polymerizable monomer (a) having an acidic group be 1 to 40 parts by weight, the content of the aliphatic polymerizable monomer (b) having no acidic group be 10 to 50 parts by weight, and the content of the water (c) be 5 to 75 parts by weight, in 100 parts by weight of the total amount of polymerizable monomers and solvents contained in the dental aqueous adhesive composition (A), and the content of the amine-based reducing agent (d1) be 0.1 to 10 parts by weight, with respect to 100 parts by weight of the total amount of polymerizable monomers in the dental aqueous adhesive composition (A); and the content of the aliphatic polymerizable monomer (b) having no acidic group be 20 to 75 parts by weight, and the content of the aromatic polymerizable monomer (e) having no acidic group be 25 to 80 parts by weight, in 100 parts by weight of the total amount of polymerizable monomers in the multi-part type dental nonaqueous curable composition (B), and the content of the powdery water-soluble reducing compound (f) be 0.1 to 3 parts by weight, the content of the organic peroxide (g) be 0.1 to 10 parts by weight, and the content of the amine-based reducing agent (d2) be 0.25 to 4 parts by weight, with respect to 100 parts by weight of the total amount of polymerizable monomers in the multi-part type dental nonaqueous curable composition (B). It is preferable that the ratio (d1/d2) of the weight of the amine-based reducing agent (d1), when the total amount of polymerizable monomers contained in the dental aqueous adhesive composition (A) is taken as 100 parts by weight, and the weight of the amine-based reducing agent (d2), when the total amount of polymerizable monomers contained in the dental nonaqueous curable composition (B) is taken as 100 parts by weight, be 0.5/1 to 35/1.

In the dental adhesive material kit of the present invention, it is preferable that the dental aqueous adhesive composition (A) further contain an aromatic polymerizable monomer (e) having no acidic group. It is preferable that the dental aqueous adhesive composition (A) further contain a photopolymerization initiator (h). It is preferable that the dental aqueous adhesive composition (A) further contain a filler (i). It is preferable that the dental nonaqueous curable composition (B) further contain the filler (i).

In the dental adhesive material kit of the present invention, it is preferable that the amine-based reducing agents (d1) and (d2) each be an aromatic amine having no electron-withdrawing group on its aromatic ring. It is preferable that the powdery water-soluble reducing compound (f) be sulfite or bisulfate in powder form.

It is preferable that the dental aqueous adhesive composition (A) be a one-component dental adhesive agent.

Suitably, the dental adhesive material kit of the present invention is a dental material kit for core construction.

Advantageous Effects of Invention

According to the dental adhesive material kit of the present invention, excellent bond durability to tooth structure such as dentin can be achieved.

DESCRIPTION OF EMBODIMENTS

The dental adhesive material kit of the present invention is characterized by including a dental aqueous adhesive composition (A) and a multi-part type dental nonaqueous curable composition (B), in which the dental aqueous adhesive composition (A) contains a polymerizable monomer (a) having an acidic group, an aliphatic polymerizable monomer (b) having no acidic group, water (c), and an amine-based reducing agent (d1) containing no sulfur atom, as essential components, and the multi-part type dental nonaqueous curable composition (B) contains an aliphatic polymerizable monomer (b) having no acidic group, an aromatic polymerizable monomer (e) having no acidic group, a powdery water-soluble reducing compound (f) containing a sulfur atom, an organic peroxide (g), and an amine-based reducing agent (d2) containing no sulfur atom, as essential components.

As a result of intensive studies by the inventors, it has been found that high bond durability can be achieved according to a two-step curing system composed of an aqueous adhesive composition that contains the amine-based reducing agent (d1) serving as a reducing agent of a redox polymerization initiator, and a nonaqueous curable composition that contains the organic peroxide (g) serving as an oxidizing agent of the redox polymerization initiator, and the powdery water-soluble reducing compound (I) and the amine-based reducing agent (d2) each serving as a reducing agent of the redox polymerization initiator.

First, a dental aqueous adhesive composition (A) is described in detail. A polymerizable monomer (a) having an acidic group is contained in the adhesive composition (A). The polymerizable monomer (a) having an acidic group to be used for the present invention accelerates the decalcification of tooth structure as well as improves the adhesive properties to tooth structure.

As the polymerizable monomer (a) having an acidic group to be used for the present invention, for example, there can be mentioned a polymerizable monomer having at least one acidic group, such as a phosphate group, a pyrophosphate group, a thiophosphate group, a phosphonate group, a carboxylic acid group, and a sulfonate group, and at least one polymerizable group, such as an acryloyl group, a methacryloyl group, a vinyl group, and a styrene group. One having an acryloyl group or a methacryloyl group as a polymerizable group is preferable. The polymerizable monomer (a) having an acidic group can be used alone or appropriately in combination of two or more kinds thereof. Specific examples of the polymerizable monomer (a) having an acidic group are shown below. It should be noted that methacryloyl and acryloyl are hereinafter collectively referred to as (meth)acryloyl.

Examples of the polymerizable monomer having a phosphate group include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl 2-bromoethyl hydrogen phosphate, 2-methacryloyloxyethyl(4-methoxyphenyl)hydrogen phosphate, 2-methacryloyloxypropyl(4-methoxyphenyl)hydrogen phosphate, and acid chlorides, alkali metal salts and amine salts thereof.

Examples of the polymerizable monomer having a pyrophosphate group include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts and amine salts thereof.

Examples of the polymerizable monomer having a thiophosphate group include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyicosyl dihydrogen thiophosphate, and acid chlorides, alkali metal salts and ammonium salts thereof.

Examples of the polymerizable monomer having a phosphonate group include 2-(meth)acryloyloxyethylphenyl phosphonate, 5-(meth)acryloyloxypentyl-3-phosphonopropyonate, 6-(meth)acryloyloxyhexyl-3-phosphonopropyonate, 10-(meth)acryloyloxydecyl-3-phosphonopropyonate, 6-(meth)acryloyloxyhexyl-3-phosphonoacetate, 10-(meth)acryloyloxydecyl-3-phosphonoacetate, and acid chlorides, alkali metal salts and ammonium salts thereof.

Examples of the polymerizable monomer having a carboxylic acid group include a monofunctional polymerizable monomer having one carboxyl group or an acid anhydride group thereof in a molecule and a monofunctional polymerizable monomer having a plurality of carboxyl groups or an acid anhydride group thereof in a molecule.

Examples of the monofunctional polymerizable monomer having one carboxyl group or an acid anhydride group thereof in a molecule include (meth)acrylic acid, N-(meth)acryloyl glycine, N-(meth)acryloyl aspartic acid, 2-(meth)acryloyloxyethyl hydrogen succinate, 2-(meth)acryloyloxyethyl hydrogen phthalate, 2-(meth)acryloyloxyethyl hydrogen malate, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, and compounds obtained by converting the carboxyl groups of these compounds into acid anhydride groups.

Examples of the monofunctional polymerizable monomer having a plurality of carboxyl groups or an acid anhydride group thereof in a molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, 6-(meth)acryloyloxyethylnaphthalene-1,2,6-tricarboxylic acid anhydride, 6-(meth)acryloyloxyethylnaphthalene-2,3,6-tricarboxylic acid anhydride, 4-(meth)acryloyloxyethylcarbonylpropionoyl-1,8-naphthalic acid anhydride, and 4-(meth)acryloyloxyethylnaphthalene-1,8-tricarboxylic acid anhydride.

Examples of the polymerizable monomer having a sulfonate group include 2-(meth)acrylamide-2-methylpropanesulfonic acid, styrenesulfonic acid, and 2-sulfoethyl(meth)acrylate.

Among the above-mentioned examples of the polymerizable monomer (a) having an acidic group, 10-(meth)acryloyloxydecyl dihydrogen phosphate, 4-(meth)acryloyloxyethyl trimellitate anhydride, 4-(meth)acryloyloxyethyl trimellitate, 11-(meth)acryloyloxyundecane-1,1-dicarboxylic acid, and a mixture of 2-methacryloyloxyethyl dihydrogen phosphate and bis(2-methacryloyloxyethyl)hydrogen phosphate are preferable, and 10-(meth)acryloyloxydecyl dihydrogen phosphate is more preferable, because good adhesion strength can be obtained when the composition is used as a dental adhesive agent.

In the dental adhesive material kit of the present invention, the content of the polymerizable monomer having an acidic group in the adhesive composition (A) is preferably 1 to 40 parts by weight, more preferably 5 to 30 parts by weight, further preferably 10 to 20 parts by weight, in 100 parts by weight of the total amount of polymerizable monomers and solvents contained in the adhesive composition (A). It should be noted that the total amount of polymerizable monomers and solvents means the total amount of the polymerizable monomer (a) having an acidic group, the aliphatic polymerizable monomer (b) having no acidic group, the aromatic polymerizable monomer (e) having no acidic group, the water (c), and an organic solvent.

The aliphatic polymerizable monomer (b) having no acidic group is contained in the adhesive composition (A). The aliphatic polymerizable monomer (b) having no acidic group to be used for the present invention penetrates into tooth structure, and thus enhances the polymerization degree of a cured product to improve the adhesiveness.

As the aliphatic polymerizable monomer (b) having no acidic group, one of a polymerizable monomer having no aromatic ring and no acidic group (such as a phosphate group, a pyrophosphate group, a thiophosphate group, a phosphonate group, a carboxylic acid group, and a sulfonate group) can be used, or two or more kinds thereof can be used in combination. Examples of the aliphatic polymerizable monomer (b) having no acidic group include aliphatic esters of an organic acid, such as alpha-cyanoacrylic acid, (meth)acrylic acid, alpha-halogenated acrylic acid, crotonic acid, sorbic acid, maleic acid, and itaconic acid, (meth)acrylamide and (meth)acrylamide derivatives, vinyl esters, vinyl ethers, and mono-N-vinyl derivatives. Above all, aliphatic (meth)acrylic acid ester and aliphatic (meth)acrylamide are suitably used from the viewpoints of the mechanical properties, the water resistance, and the coloration resistance, etc., of a cured product and the curing speed.

Specific examples of aliphatic (meth)acrylamide and aliphatic (meth)acrylic acid ester having no acidic group are shown below. In the following description, the terms "monofunctional", "bifunctional", and "at least trifunctional" respectively mean to have one, two, and three or more radical polymerizable groups such as (meth)acryloyl group.

Monofunctional aliphatic (meth)acrylic acid esters and aliphatic (meth)acrylamides: methyl(meth)acrylate, ethyl(meth)acrylate, propyl(meth)acrylate, isopropyl(meth)acrylate, butyl(meth)acrylate, isobutyl(meth)acrylate, lauryl (meth)acrylate, 2-(N,N-dimethylamino)ethyl(meth)acrylate, 2,3-dibromopropyl(meth)acrylate, 2-hydroxyethyl(meth) acrylate, 3-hydroxypropyl(meth)acrylate, 6-hydroxyhexyl (meth)acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, N,N-(dihydroxyethyl)(meth)acrylamide, etc.

Further, (meth)acrylic acid ester having a fluorocarbon chain represented by the following general formula (I) may be contained therein.

$$CH_2=C(R^1)COO-R^2-Rf \qquad (I)$$

(In the formula, $R^1$ denotes a hydrogen atom or a methyl group, $R^2$ denotes an alkylene group, Rf denotes a perfluoro alkyl group, $R^2$—Rf involves 4 to 10 carbon atoms, and fluorine atoms account for at least 50% in the number of the atoms bound to the carbon atoms of $R^2$—Rf.)

Bifunctional aliphatic (meth)acrylic acid esters: ethylene glycol di(meth)acrylate, triethylene glycol di(meth)acrylate, polyethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 1,2-bis[3-(meth)acryloyloxy-2-hydroxypropoxy] ethane, pentaerythritol di(meth)acrylate, 1,2-bis(3-methacryloyloxy-2-hydroxypropoxy)ethane, 2-hydroxy-1,3-dimethacryloyloxypropane, [2,2,4-trimethylhexamethylene bis(2-carbamoyloxyethyl)] dimethacrylate, etc.

At least trifunctional aliphatic (meth)acrylic acid esters: trimethylolpropane tri(meth)acrylate, trimethylolethane tri (meth)acrylate, tetramethylolmethane tri(meth)acrylate, pentaerythritol tetra(meth)acrylate, N,N'-(2,2,4-trimethylhexamethylene)bis[2-(aminocarboxy)propane-1,3-diol] tetramethacrylate, 1,7-diacryloyloxy-2,2,6,6-tetraacryloyloxymethyl-4-oxyheptane, etc.

Among the above-mentioned examples of the aliphatic polymerizable monomer (b) having no acidic group, one containing a hydroxyl group is preferable. 1,2-bis(3-methacryloyloxy-2-hydroxypropoxy)ethane, 2-hydroxyethyl(meth) acrylate, and 2-hydroxy-1,3-dimethacryloyloxypropane are preferable. Further, neopentyl glycol di(meth)acrylate also can be used preferably.

In the dental adhesive material kit of the present invention, the content of the aliphatic polymerizable monomer (b) having no acidic group in the adhesive composition (A) is preferably 10 to 50 parts by weight, more preferably 15 to 45 parts by weight, further preferably 20 to 40 parts by weight, in 100 parts by weight of the total amount of polymerizable monomers and solvents contained in the adhesive composition (A).

The water (c) is contained in the adhesive composition (A) of the present invention. The water (c) contributes to promoting the penetration of a composition into tooth structure. Further, the water (c) also functions as a solvent to dissolve the powdery water-soluble reducing compound (f).

In the dental adhesive material kit of the present invention, the content of the water (c) in the adhesive composition (A) is preferably 5 to 75 parts by weight, more preferably 10 to 60 parts by weight, further preferably 15 to 45 parts by weight, in 100 parts by weight of the total amount of polymerizable monomers and solvents contained in the adhesive composition (A).

The amine-based reducing agent (d1) containing no sulfur atom is contained in the dental adhesive material kit of the present invention. The amine-based reducing agent (d1) in the adhesive composition (A) to be used for the present invention is a reducing agent component of a redox polymerization initiator. It accelerates redox polymerization at the interface of tooth structure together with the organic peroxide (g) when the multi-part type dental nonaqueous curable composition (B) is applied thereto, and thus contributes to high adhesive properties and bond durability.

As the amine-based reducing agent (d1), an aromatic amine having no electron-withdrawing group on its aromatic ring can be mentioned.

Examples of the aromatic amine having no electron-withdrawing group on its aromatic ring include a compound in which no hydrogen atom on the aromatic ring of aromatic amine is substituted by an electron-withdrawing group such as a carboxylic acid group, a carboxylic acid ester group, a nitrile group, and a halogen group. Specific examples thereof include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, and N,N-dimethyl-3,5-di-t-butylaniline. As the aromatic amine having no electron-withdrawing group on its aromatic ring, any one of these may be used alone, or two or more of them may be used in combination.

Among the above-mentioned examples of the amine-based reducing agent (d1), N,N-dimethyl-p-toluidine and N,N-di (2-hydroxyethyl)-p-toluidine are preferable.

In the present invention, the content of the amine-based reducing agent (d1) is preferably 0.1 to 10 parts by weight, with respect to 100 parts by weight of the total amount of polymerizable monomers in the adhesive composition (A). When the content is 0.1 part by weight or more, the bond strength is prevented from decreasing, and more suitably, the content is 0.25 part by weight or more. Meanwhile, when the content exceeds 10 parts by weight, the bond strength may possibly decrease, and there may be cases where sufficient working time is not obtained. More suitably, the content is 7.5 parts by weight or less. Accordingly, from the above-mentioned viewpoints, the content of the amine-based reducing agent (d1) is more preferably 0.25 to 7.5 parts by weight, further preferably 0.5 to 5 parts by weight, with respect to 100 parts by weight of the total amount of polymerizable monomers in the adhesive composition (A). It should be noted that the total amount of polymerizable monomers means the total amount of the polymerizable monomer (a) having an acidic group, the aliphatic polymerizable monomer (b) having no acidic group, and the aromatic polymerizable monomer (e) having no acidic group.

In the adhesive composition (A) to be used for the present invention, the aromatic polymerizable monomer (e) having no acidic group is preferably contained.

As the aromatic polymerizable monomer (e) having no acidic group, a (meth)acrylate monomer having no acidic group but having an aromatic ring and a hydroxyl group, and a (meth)acrylate monomer having an aromatic ring but having no acidic group and no hydroxyl group can be mentioned.

The (meth)acrylate monomer having no acidic group but having an aromatic ring and a hydroxyl group is not specifically limited as long as it is a (meth)acrylate monomer having no acidic group but having an aromatic ring and a hydroxyl group. The number of the aromatic ring and the number of the hydroxyl group are independent from each other. The number of each functional group to be contained therein is at least one. Examples of such a compound include a (meth)acrylate monomer having a bisphenol A skeleton and having a hydroxyl group. Specific examples thereof include 2,2-bis[4-(3-(meth)acryloyloxy)-2-hydroxypropoxyphenyl]propane (commonly known as "Bis-GMA"), 2-{4-[3-(meth)acryloyloxy-2-hydroxypropoxy]phenyl}-2-{4-[2,3-di(meth)acryloyloxypropoxy]phenyl}propane (commonly known as "Bis3"), 2-{4-[3-(meth)acryloyloxy-2-hydroxypropoxy]phenyl}-2-[4-(meth)acryloyloxydiethoxyphenyl]propane, 2-{4-[(meth)acryloyloxy-2-hydroxypropoxy]phenyl}-2-[4-(meth)acryloyloxytriethoxyphenyl]propane, and 2-{4-[3-(meth)acryloyloxy-2-hydroxypropoxy]phenyl}-2-[4-(meth)acryloyloxydipropoxyphenyl]propane. One of these may be used alone, or two or more of these may be used appropriately in combination.

The (meth)acrylate monomer having an aromatic ring but having no acidic group and no hydroxyl group is not specifically limited as long as it is a (meth)acrylate monomer having an aromatic ring but having no acidic group and no hydroxyl group. The (meth)acrylate monomer needs to have at least one aromatic ring. Examples of such a compound include a (meth)acrylate monomer having a bisphenol A skeleton but having no hydroxyl group. Specific examples thereof include 2,2-bis((meth)acryloyloxyphenyl)propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane.

Among these, as the aromatic polymerizable monomer (e) having no acidic group to be used for the adhesive composition (A), a (meth)acrylate monomer having no acidic group but having an aromatic ring and a hydroxyl group is preferable. Bis-GMA is preferable for achieving excellent mechanical strength after curing.

In the dental adhesive material kit of the present invention, the content of the aromatic polymerizable monomer (e) having no acidic group in the adhesive composition (A) is preferably 15 to 45 parts by weight, more preferably 20 to 40 parts by weight, further preferably 25 to 35 parts by weight, in 100 parts by weight of the total amount of polymerizable monomers and solvents contained in the adhesive composition (A).

In the dental adhesive material kit of the present invention, a photopolymerization initiator (h) is preferably contained in the adhesive composition (A) so that photocurability is imparted.

Examples of the photopolymerization initiator (h) include (bis)acylphosphine oxides, thioxanthones or the quaternary ammonium salts of thioxanthones, ketals, alpha-diketones, coumarins, anthraquinones, benzoin alkyl ether compounds, and alpha-amino ketone compounds. Specific examples thereof are disclosed in WO 2008/087977 A1.

Among these photopolymerization initiators, it is preferable to use at least one selected from the group consisting of (bis)acylphosphine oxides and salts thereof, and alpha-diketones. This allows a composition to have excellent photocurability in visible and near-ultraviolet regions and to exhibit sufficient photocurability when using whichever light source of halogen lamp, light emitting diode (LED), xenon lamp.

The content of the photopolymerization initiator (h) is not specifically limited, but preferably 0.1 to 10 parts by weight, with respect to 100 parts by weight of the total amount of polymerizable monomers in the adhesive composition (A), in view of photocurability.

When using the photopolymerization initiator (h), a known polymerization accelerator may be used in combination for the purpose of accelerating photopolymerization. Accordingly, the adhesive composition (A) may contain a polymerization accelerator.

A filler (i) is preferably contained in the adhesive composition (A) in order to improve adhesive properties, coating properties, fluidity, X-ray opacity, and mechanical strength. Examples of the filler (i) include an inorganic filler, an organic filler, and a composite filler of an inorganic filler and an organic filler.

Examples of the inorganic filler include: silica; a mineral containing silica as a base, such as kaoline, clay, isinglass, and mica; and ceramics and glasses containing silica as a base and containing $Al_2O_3$, $B_2O_3$, $TiO_2$, $ZrO_2$, BaO, $La_2O_3$, SrO, ZnO, CaO, $P_2O_5$, $Li_2O$, $Na_2O$, etc. As the glasses, lanthanum glass, barium glass, strontium glass, soda glass, lithium borosilicate glass, zinc glass, fluoroaluminosilicate glass, borosilicate glass, and bioglass are used suitably. Also, crystalline quartz, hydroxyapatite, alumina, titanium oxide, yttrium oxide, zirconia, calcium phosphate, barium sulphate, aluminum hydroxide, sodium fluoride, potassium fluoride, sodium monofluorophosphate, lithium fluoride, and ytterbium fluoride are used suitably.

Examples of the composite filler of an inorganic filler and an organic filler include a composite filler obtained by dispersing an inorganic filler in an organic filler, and an inorganic/organic composite filler obtained by coating an inorganic filler with various polymerizable monomers.

In order to enhance curability, mechanical strength, and coating properties, the filler (i) may be used after being subjected to a surface pretreatment with a known surface-treating agent such as a silane coupling agent. Examples of the surface-treating agent include vinyltrimethoxysilane, vinyltriethoxysilane, vinyltrichlorosilane, vinyltri(beta-methoxyethoxy)silane, gamma-methacryloyloxypropyltrimethoxysilane, gamma-glycidoxypropyltrimethoxysilane, gamma-mercaptopropyltrimethoxysilane, and gamma-aminopropyltriethoxysilane.

As the filler (i) to be used in the adhesive composition (A), a fine particle filler having a primary particle size of 0.001 to 0.1 μm is preferable in view of adhesiveness and coating properties. Specific examples thereof include "Aerosil OX50", "Aerosil 50", "Aerosil 200", "Aerosil 380", "Aerosil R972", and "Aerosil 130" (each of which is a product name, manufactured by Japan Aerosil Inc.).

As the filler (i), one of these may be added alone, or two or more kinds of these may be added in combination.

The content of the filler (i) is preferably in the range of 0.1 to 30 parts by weight, more preferably in the range of 0.5 to 20 parts by weight, most preferably in the range of 1 to 10 parts by weight, with respect to 100 parts by weight of the total amount of polymerizable monomers in the adhesive composition (A).

In the dental adhesive material kit of the present invention, a water-soluble organic solvent may be contained in the adhesive composition (A) in order to improve adhesiveness, coating properties, penetrability into tooth structure, and the solubility of the polymerizable monomer (a) having an acidic group and the aliphatic polymerizable monomer (b) having no acidic group in the water (c). As the water-soluble organic solvent, an organic solvent that has a boiling point of 150° C. or less under normal pressure, and that can be dissolved in water with a solubility in water at 25° C. of at least 5 wt %, more preferably at least 30 wt %, most preferably with a solubility capable of being dissolved in an arbitrary ratio, is generally used. Above all, a water-soluble organic solvent having a boiling point of 100° C. or less under normal pressure is preferable. Specific examples thereof include ethanol, methanol, 1-propanol, isopropyl alcohol, acetone, methyl ethyl ketone, 1,2-dimethoxyethane, 1,2-diethoxyethane, and tetrahydrofuran.

As a water-soluble organic solvent, one of these may be added alone, or two or more kinds of these may be added in combination. When the content of the water-soluble organic solvent is excessively large, the adhesiveness may decrease. The content of the water-soluble organic solvent is preferably in the range of 1 to 70 parts by weight, more preferably in the range of 5 to 50 parts by weight, most preferably in the range of 7.5 to 30 parts by weight, in 100 parts by weight of the total amount of polymerizable monomers and solvents contained in the adhesive composition (A).

In the dental adhesive material kit of the present invention, the adhesive composition (A) is preferably of one-component type because of no need for mixing and ease of operation.

Subsequently, the multi-part type dental nonaqueous curable composition (B) is described.

The multi-part type dental nonaqueous curable composition (B) contains the aliphatic polymerizable monomer (b) having no acidic group, the aromatic polymerizable monomer (e) having no acidic group, the powdery water-soluble reducing compound (f) containing a sulfur atom, the organic peroxide (g), and the amine-based reducing agent (d2) containing no sulfur atom.

As the aliphatic polymerizable monomer (b) having no acidic group to be contained in the multi-part type dental nonaqueous curable composition (B), those mentioned for the aliphatic polymerizable monomer (b) having no acidic group to be contained in the adhesive composition (A) can be used.

Among the above-mentioned examples of the aliphatic polymerizable monomer (b) having no acidic group, at least bifunctional polymerizable monomers are preferable, and 1,2-bis(3-methacryloyloxy-2-hydroxypropoxy)ethane, neopentyl glycol dimethacrylate, and triethylene glycol dimethacrylate are more preferable, since the operability and the paste properties of the composition and the mechanical strength of the cured product are excellent.

The content of the aliphatic polymerizable monomer (b) having no acidic group in the curable composition (B) is preferably 20 to 75 parts by weight, more preferably 25 to 70 parts by weight, in 100 parts by weight of the total amount of polymerizable monomers in the curable composition (B).

As the aromatic polymerizable monomer (e) having no acidic group to be contained in the multi-part type dental nonaqueous curable composition (B), those mentioned for the aromatic polymerizable monomer (e) having no acidic group to be contained in the adhesive composition (A) can be used.

Among them, 2,2-bis[4-(3-(meth)acryloyloxy-2-hydroxypropoxyphenyl]propane and 2,2-bis(4-(meth)acryloyloxypolyethoxyphenyl)propane are preferable because excellent strength can be obtained when the composition is used as a material for core construction. Among 2,2-bis(4-(meth)acryloyloxypolyethoxyphenyl)propane, a compound in which the average number of moles of added ethoxy group is 2.6 (commonly known as "D2.6E") is preferable.

The content of the aromatic polymerizable monomer (e) having no acidic group in the curable composition (B) is preferably 25 to 80 parts by weight, more preferably 30 to 75 parts by weight, in 100 parts by weight of the total amount of polymerizable monomers in the curable composition (B).

In the multi-part type dental nonaqueous curable composition (B), the powdery water-soluble reducing compound (f) containing a sulfur atom is contained. The powdery water-soluble reducing compound (f) is a reducing agent component of the redox polymerization initiator. The powdery water-soluble reducing compound (f) is powder dispersed in the nonaqueous curable composition. When the curable composition (B) is applied to tooth structure treated with the adhesive composition (A), the powdery water-soluble reducing compound (f) is dissolved in the water contained in the tooth structure and the adhesive composition (A), thereby accelerating the curing reaction efficiently at the bonding interface, together with the amine-based reducing agent (d1) in the adhesive composition (A).

The term "water-soluble" in the present invention means to have a solubility in water at room temperature (25° C.) of 0.5 mg/100 mL or more. As the powdery water-soluble reducing compound (f), one having this solubility of 1 mg/100 mL or more is preferable. Examples of the powdery water-soluble reducing compound (f) include sulfite, bisulfate, pyrosulfite, thiosulfate, thionate, dithionite, etc., each in powder form. Among these examples, sulfite and bisulfate each in powder form are preferable, and above all, sodium sulfite, potassium sulfite, calcium sulfite, ammonium sulfite, sodium bisulfite, and potassium hydrogensulfite each in powder form are most preferable, because of low solubility in the aliphatic polymerizable monomer (b) having no acidic group and the aromatic polymerizable monomer (e) having no acidic group, high solubility in water, and high performance as a reducing agent. The dispersion state of the powdery water-soluble reducing compound (f) in the composition can be checked as follows. After the composition is cured in the absence of water, the cured product is fractured, and the fractured section is subjected to an analysis using a micro-energy dispersive X-ray fluorescence spectrometer.

The average particle size of the powdery water-soluble reducing compound (f) is not limited, but is preferably 500 μm or less, more preferably 100 μm or less, because excessively large average particle size tends to cause sedimentation. On the other hand, excessively small average particle size makes the specific surface area of the powder excessively large, which causes a reduction in the amount of the powdery water-soluble reducing compound (f) that can be dispersed in the aliphatic polymerizable monomer (b) having no acidic group and the aromatic polymerizable monomer (e) having no acidic group. Thus, the average particle size of the powdery water-soluble reducing compound (f) is preferably 0.01 μm or more. That is, the average particle size of the powdery water-soluble reducing compound (f) is preferably in the range of 0.01 to 500 μm, more preferably in the range of 0.01 to 100 μm.

The shape of the powdery water-soluble reducing compound (f) is not particularly limited, and examples thereof include various shapes such as a spherical shape, a needle shape, a plate shape, and a crushed shape. The powdery water-soluble reducing compound (f) can be produced by a known method such as grinding and freeze drying.

In the present invention, the content of the powdery water-soluble reducing compound (f) is preferably 0.1 to 3 parts by weight, with respect to 100 parts by weight of the total amount of polymerizable monomers in the curable composition (B). When it is less than 0.1 part by weight, there is a possibility of failure to obtain high adhesive properties. More suitably, the content of the powdery water-soluble reducing compound (f) is at least 0.2 part by weight. Meanwhile, when it exceeds 3 parts by weight, there is a possibility of reduction in the mechanical strength of the cured product. More suitably, the content of the powdery water-soluble reducing compound (f) is not more than 2.5 parts by weight. Accordingly, from the above-mentioned viewpoints, the content of the powdery water-soluble reducing compound (f) is more preferably 0.2 to 2.5 parts by weight, further preferably 0.3 to 2 parts by weight, with respect to 100 parts by weight of the total amount of polymerizable monomers in the curable composition (B).

In the dental adhesive material kit of the present invention, the organic peroxide (g) is contained in the multi-part type dental nonaqueous curable composition (B). The organic peroxide (g) is an oxidizing agent component of the redox polymerization initiator.

Examples of the organic peroxide (g) include diacyl peroxides, peroxyesters, peroxycarbonates, dialkyl peroxides, peroxyketals, ketone peroxides, and hydroperoxides.

Specific examples of diacyl peroxides include benzoyl peroxide, 2,4-dichlorobenzoyl peroxide, m-toluoyl peroxide, and lauroyl peroxide.

Specific examples of peroxyesters include t-butylperoxybenzoate, bis-t-butylperoxyisophthalate, and t-butylperoxy-2-ethyl hexanoate.

Specific examples of peroxycarbonates include t-butylperoxyisopropyl carbonate.

Specific examples of dialkyl peroxides include dicumyl peroxide, di-t-butyl peroxide, and 2,5-dimethyl-2,5-di(benzoylperoxy)hexane.

Specific examples of peroxyketals include 1,1-bis(t-butylperoxy)-3,3,5-trimethylcyclohexane, 1,1-bis(t-butylperoxy)cyclohexane, and 1,1-bis(t-hexylperoxy)cyclohexane.

Specific examples of ketone peroxides include methyl ethyl ketone peroxide, cyclohexanone peroxide, and methyl acetoacetate peroxide.

Specific examples of hydroperoxides include t-butyl hydroperoxide, cumene hydroperoxide, and diisopropyl benzene hydroperoxide.

The content of the organic peroxide (g) in the curable composition (B) is preferably 0.1 to 10 parts by weight, with respect to 100 parts by weight of the total amount of polymerizable monomers in the curable composition (B). The content of the organic peroxide (g) of less than 0.1 part by weight may slow the curing. More suitably, the content of the organic peroxide (g) is at least 0.2 part by weight. The content thereof exceeding 10 parts by weight may accelerate the curing excessively, which may result in failure to obtain high adhesive properties. More suitably, the content of the organic peroxide (g) is not more than 7.5 parts by weight. Accordingly, from the above-mentioned viewpoints, the content of the organic peroxides (g) is more preferably 0.2 to 7.5 parts by weight, further preferably 0.3 to 5 parts by weight, with respect to 100 parts by weight of the total amount of polymerizable monomers in the curable composition (B).

In the curable composition (B), the amine-based reducing agent (d2) containing no sulfur atom is contained. The amine-based reducing agent (d2) is a reducing agent component of the redox polymerization initiator. The amine-based reducing agent (d2) contributes to the curing reaction of the curable composition (B) by undergoing a redox reaction with the organic peroxide (g), and improves the durability of the mechanical properties (such as durability of flexural strength) of the cured product of the curable composition (B).

As the amine-based reducing agent (d2), those mentioned for the amine-based reducing agent (d1) to be contained in the adhesive composition (A) can be used.

In the present invention, the content of the amine-based reducing agent (d2) is preferably 0.25 to 4 parts by weight, with respect to 100 parts by weight of the total amount of polymerizable monomers in the curable composition (B). The content of the amine-based reducing agent (d2) of less than 0.25 part by weight may slow the curing. More suitably, the content of the amine-based reducing agent (d2) is at least 0.3 part by weight. Meanwhile, the content thereof exceeding 4 parts by weight may accelerate the curing excessively, which may result in failure to obtain high adhesive properties. More suitably, the content of the amine-based reducing agent (d2) is not more than 3.5 parts by weight. Accordingly, from the above-mentioned viewpoints, the content of the amine-based reducing agent (d2) is more preferably 0.3 to 3.5 parts by weight, further preferably 0.4 to 3 parts by weight, with respect to 100 parts by weight of the total amount of polymerizable monomers in the curable composition (B).

In the dental adhesive material kit of the present invention, the ratio (d1/d2) of the weight of the amine-based reducing agent (d1), when the total amount of polymerizable monomers contained in the adhesive composition (A) is taken as 100 parts by weight, and the weight of the amine-based reducing agent (d2), when the total amount of polymerizable monomers contained in the curable composition (B) is taken as 100 parts by weight, is preferably 0.5/1 to 35/1, in order to obtain high adhesive properties to tooth structure. This weight ratio of less than 0.5/1 may make it difficult to obtain high adhesive properties and high bond durability, while the weight ratio of more than 35/1 may slow the curing of the curable composition (B). It can be presumed that, when the amine-based reducing agent (d1) is contained in the adhesive composition (A), high bond strength is obtained because polymerization proceeds at a portion where the adhesive composition (A) has penetrated into the tooth surface.

The multi-part type dental curable composition (B) to be used for the present invention is nonaqueous. The term "nonaqueous" means that "substantially no water is contained". The phrase "substantially no water is contained" means that no water is positively added, but a slight amount of water that has been unavoidably incorporated is allowed to be contained. In terms of specific numerical values, the phrase "substantially no water is contained" means that the content of water is not more than 5 parts by weight, preferably not more than 3 parts by weight, more preferably not more than 1 part by weight, with respect to 100 parts by weight of the total amount of polymerizable monomers in the curable composition (B).

In the curable composition (B), the photopolymerization initiator (h) is preferably contained so that photocurability is imparted.

As the photopolymerization initiator (h), those mentioned for the photopolymerization initiator (h) for the adhesive composition (A) can be used.

The content of the photopolymerization initiator (h) is not specifically limited, but preferably 0.01 to 10 parts by weight, more preferably 0.10 to 3 parts by weight, with respect to 100 parts by weight of the total amount of polymerizable monomers in the curable composition (B), from the viewpoint of photocurability.

It should be noted that a known polymerization accelerator may be used in combination when using the photopolymerization initiator (h), for the purpose of accelerating the photopolymerization. Accordingly, the curable composition (B) may contain a polymerization accelerator.

In the dental adhesive material kit of the present invention, a filler is preferably contained in the curable composition (B) in order to enhance the mechanical strength after curing.

As the filler (i) to be used in the curable composition (B), those mentioned for the filler (i) for the adhesive composition (A) can be used.

Preferable examples of the filler (i) to be used in the curable composition (B) include silica, lanthanum glass, barium glass, strontium glass, soda glass, lithium borosilicate glass, zinc glass, fluoroaluminosilicate glass, borosilicate glass, bioglass, crystal quartz, alumina, titanium oxide, yttrium oxide, and zirconia.

The content of the filler (i) is not specifically limited, but preferably 50 to 750 parts by weight, more preferably 75 to 700 parts by weight, with respect to 100 parts by weight of the total amount of polymerizable monomers in the curable composition (B), from the viewpoints of the mechanical strength and the operability.

The dental nonaqueous curable composition (B) is dividedly packed so as not to cause a redox reaction of the organic peroxide (g) with the powdery water-soluble reducing compound (f) and the amine-based reducing agent (d2) during storage. Suitably, the dental nonaqueous curable composition (B) is dividedly packed into two parts, one part of which contains the organic peroxide (g), and the other part of which contains the powdery water-soluble reducing compound (f) and the amine-based reducing agent (d2). At this time, polymerizable monomers are preferably contained in both parts so that the two parts in paste form can be obtained.

In the dental adhesive material kit of the present invention, a known water-soluble fluoride compound that releases fluorine ions may be contained in the adhesive composition (A) and/or the curable composition (B) in an amount that does not reduce the adhesive properties. Examples of the water-soluble fluoride compound include lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminum fluoride, manganese fluoride, copper fluoride, lead fluoride, silver fluoride, antimony fluoride, cobalt fluoride, bismuth fluoride, tin fluoride, diammine silver fluoride, sodium monofluorophosphate, potassium fluorotitanate, fluorostannate, and fluorosilicate. As the water-soluble fluoride compound, one of these may be used alone, or two or more kinds of these may be used in combination. In the case of adding the water-soluble fluoride compound, the water-soluble fluoride compound is preferably added after being micronized by a method disclosed, for example, in JP 2 (1990)-258602 A, or after being coated with polysiloxane by a method disclosed, for example, in JP 10 (1998)-36116 A.

Further, in the dental adhesive material kit of the present invention, a known additive may be contained in the adhesive composition (A) and the curable composition (B) within a range that does not decrease the performance. Examples of such an additive include a polymerization inhibitor, an antioxidant, a pigment, a dye, an ultraviolet absorber, an organic solvent, a thickener, etc.

In the dental adhesive material kit of the present invention, the adhesive composition (A) is first applied to a bonding target, and then the curable composition (B) is applied thereto. In the dental adhesive material kit of the present invention, the adhesive composition (A) may be formed as a primer, or may be formed as an adhesive agent. As a use embodiment of the dental adhesive material kit of the present invention, the following (1) and (2) can be mentioned, for example: (1) to use the adhesive composition (A) as a primer while using the curable composition (B) as an adhesive agent; and (2) to use the adhesive composition (A) as a one-component adhesive agent while using the curable composition (B) as a composite resin.

In the case of using the adhesive composition (A) as a primer, the adhesive composition (A) preferably contains 1 to 40 parts by weight of (a), 20 to 50 parts by weight of (b), and 30 to 75 parts by weight of (c), in 100 parts by weight of the total amount of polymerizable monomers and solvents, and preferably contains 0.1 to 10 parts by weight of (d1), with respect to 100 parts by weight of the total amount of polymerizable monomers.

In the case of using the curable composition (B) as an adhesive agent, the curable composition (B) preferably contains 30 to 75 parts by weight of (b), and 25 to 70 parts by weight of (e), in 100 parts by weight of the total amount of polymerizable monomers, and preferably contains 0.1 to 3 parts by weight of (f), 0.1 to 10 parts by weight of (g), and 0.25 to 4 parts by weight of (d2), with respect to 100 parts by weight of the total amount of polymerizable monomers.

In the case of using the adhesive composition (A) as a one-component adhesive agent, the adhesive composition (A) preferably contains 1 to 40 parts by weight of (a), 10 to 40 parts by weight of (b), 5 to 50 parts by weight of (c), 15 to 40 parts by weight of (e), and 5 to 50 parts by weight of the water-soluble organic solvent, in 100 parts by weight of the total amount of polymerizable monomers and solvents, and preferably contains 0.1 to 10 parts by weight of (d1), 0.1 to 10 parts by weight of (h), and 1 to 10 parts by weight of (i), with respect to 100 parts by weight of the total amount of polymerizable monomers.

In the case of using the curable composition (B) as a composite resin, the curable composition (B) preferably contains 20 to 65 parts by weight of (b) and 35 to 80 parts by weight of (e), in 100 parts by weight of the total amount of polymerizable monomers, and preferably contains 0.1 to 3 parts by weight of (f), 0.1 to 10 parts by weight of (g), 0.25 to 4 parts by weight of (d2), and 50 to 750 parts by weight of (i), with respect to 100 parts by weight of the total amount of polymerizable monomers.

In the present invention, it is preferable to form the adhesive composition (A) as a one-component dental adhesive agent. One preferable use embodiment of the dental adhesive material kit of the present invention is the above-mentioned (2). In the use embodiment of the above-mentioned (2), the aliphatic polymerizable monomer (b) having no acidic group to be contained in the curable composition (B) preferably contains at least 60 wt % of the at least bifunctional polymerizable monomers, more preferably at least 80 wt % of the at least bifunctional polymerizable monomers, further preferably at least 90 wt % of the at least bifunctional polymerizable monomers, most preferably contains only the at least bifunctional polymerizable monomers, because the operability and the paste properties of the composition and the mechanical strength of the cured product are excellent.

According to the dental adhesive material kit of the present invention, excellent bond durability can be obtained. The dental adhesive material kit of the present invention is preferably a dental material kit for core construction. In this regard, the dental adhesive material kit is preferably used in the above-mentioned embodiment (2), so that high adhesiveness and bond durability can be obtained even in the deep part of a root canal that can be hardly reached by light.

EXAMPLES

Hereinafter, the present invention is described with reference to examples and comparative examples. However, the present invention is not limited by these examples. Abbreviations to be used hereinafter are shown below.

<Polymerizable Monomer (a) Having an Acidic Group>
MDP: 10-methacryloyloxydecyl dihydrogen phosphate
4-META: 4-methacryloyloxyethyl trimellitate anhydride
MAC-10: 11-methacryloyloxyundecane-1,1-dicarboxylic acid
4-MET: 4-methacryloyloxyethyl trimellitate
PM: mixture of 2-methacryloyloxyethyl dihydrogenphosphate and
bis(2-methacryloyloxyethyl)hydrogenphosphate
<Aliphatic Polymerizable Monomer (b) Having No Acidic Group>
HEMA: 2-hydroxyethyl methacrylate
GDMA: 2-hydroxy-1,3-dimethacryloyloxypropane
GDEMA: 1,2-bis(3-methacryloyloxy-2-hydroxypropoxy) ethane
NPG: neopentyl glycol dimethacrylate
TEGDMA: triethylene glycol dimethacrylate
<Water (c)>
Water
<Amine-Based Reducing Agents (d1), (d2)>
DEPT: N,N-di(2-hydroxyethyl)-p-toluidine
DMPT: N,N-dimethyl-p-toluidine
<Aromatic Polymerizable Monomer (e) Having No Acidic Group>
Bis-GMA: 2,2-bis[4-(3-methacryloyloxy)-2-hydroxypropoxyphenyl]propane
D2.6E: 2,2-bis(4-methacryloyloxypolyethoxyphenyl)propane
<Powdery Water-Soluble Reducing Compound (f)>
Sodium sulfite powder (average particle size: 6.1 μm)
<Organic Peroxide (g)>
BPO: benzoyl peroxide
<Photopolymerization Initiator (h)>
BAPO: bis(2,4,6-trimethylbenzoyl)phenylphosphine oxide
CQ: dl-camphorquinone
PDE: ethyl(N,N-dimethylamino)benzoate (polymerization accelerator)
<Filler (i)>
R972: fine particle silica, manufactured by Japan Aerosil Inc., silane-treated Ba glass
<Organic Solvent>
Ethanol Example 1

A dental aqueous adhesive composition having the following composition was prepared as a primer. Further, the following M-1 part and M-2 part were prepared as adhesive agents, which were combined to produce a multi-part type dental nonaqueous curable composition having a weight ratio of the two parts of 1:1. Sodium sulfite was dispersed in powder form in the composition obtained by mixing M-1 part and M-2 part. For a dental adhesive material kit composed of the dental aqueous adhesive composition and the multi-part type dental nonaqueous curable composition, the following tensile bond strength test (Q1) was conducted to determine the tensile bond strength. Further, for the multi-part type dental nonaqueous curable composition, the flexural strength test (Q2) was conducted to determine the flexural strength. Table 1 shows the results.

Dental Aqueous Adhesive Composition (P-1):

| MDP | 10 parts by weight |
| HEMA | 25 parts by weight |
| Water | 65 parts by weight |
| DEPT | 1 part by weight |

M-1 Part:

| Bis-GMA | 40 parts by weight |
| HEMA | 30 parts by weight |
| NPG | 30 parts by weight |
| BPO | 1 part by weight |

M-2 Part:

| Bis-GMA | 40 parts by weight |
| HEMA | 30 parts by weight |
| NPG | 30 parts by weight |
| DEPT | 1.5 parts by weight |

Sodium sulfite powder (average particle size: 6.1 μm) 1 part by weight

<<Tensile Bond Strength Test (Q1): Chemical Curing>>

The labial surface of a bovine mandibular incisor was ground with #80 silicon carbide paper (manufactured by NIHON KENSHI CO., LTD.) under running water to form a flat surface of dentin. The flat surface was further grounded with #1000 silicon carbide paper (manufactured by NIHON KENSHI CO., LTD.) under running water so as to be a smooth surface. An adhesive tape having a thickness of about 150 μm and being provided with a 4-mm-diameter circular hole was attached to the smooth surface, thereby defining the bonding area. Subsequently, the prepared dental aqueous adhesive composition P-1 was applied to the inside of the above-mentioned circular hole using a brush, which was left standing for 30 seconds. Thereafter, it was dried with an air syringe until the fluidity of the adhesive composition was lost. Next, a mixture of M-1 part and M-2 part was applied to the surface coated with the adhesive composition using a small brush. The coating thickness was about 100 μm. Onto the coated surface, a commercially available photopolymerization-type dental composite resin (product name "Clearfil AP-X", manufactured by KURARAY MEDICAL INC.) was mounted. After it was covered with a mold release film (product name "EVAL", manufactured by KURARAY CO., LTD.), a slide glass was mounted on and pressed against the mold release film. It was then irradiated with light using a dental visible light curing unit (product name "JET LITE 3000", manufactured by J. Morita USA) for 40 seconds to be cured. Using a commercially available dental resin cement (product name "Panavia Fluoro Cement", manufactured by KURARAY MEDICAL INC.), one end of a 7 mm diameter× 25 mm high cylindrical rod made of SUS304 was bonded to the obtained cured product, which was used as a specimen. 16 specimens were produced in total. After 1 hour from the bonding, the specimen was immersed in water at 37° C. After 24 hours, it was taken out from the water, and subjected to measurement of the tensile bond strength with a universal testing machine (manufactured by SHIMADZU CORPORATION). The measurement of the tensile bond strength was performed with a cross-head speed being set at 2 mm/min. The average of the measured values of 8 specimens was taken as the tensile bond strength.

The remaining 8 specimens bonded to dentin were further subjected to a thermal cycle load in which each specimen was immersed alternately in a water bath at 4° C. and a water bath at 60° C. each for 1 minute 4000 times, and thereafter the tensile bond strength was measured. The bond durability was evaluated from this tensile bond strength after the thermal cycle load. Table 1 shows the results.

<<Flexural Strength Test (Q2): Strength of Chemically Cured Product>>

Equal amounts of the first part and the second part of the prepared multi-part type dental nonaqueous curable composition were collected, and mixed for 30 seconds. The obtained mixture was charged into a stainless steel mold (size: 2 mm×2 mm×25 mm), and thereafter it was pressed from above and below each with a slide glass, and then allowed to stand for 1 hour in the air at 37° C. to be cured. The obtained cured product was separated from the mold, which was used as a specimen. 10 specimens were produced and deburred. The cured product was placed in water at 37° C. for 24 hours. Thereafter, the flexural strength of the cured product was measured, using a universal testing machine (product code "AGI-100", manufactured by SHIMADZU CORPORATION), with the span being set at 20 mm and the crosshead speed being set at 1 mm/min. The average of the measured values of 5 specimens was taken as the flexural strength. The remaining 5 specimens were further placed in water at 70° C. for one week, and thereafter subjected to measurement of the flexural strength. This was taken as the durability of flexural strength.

Example 2

P-2 part having the following composition was prepared using 0.2 part by weight of DEPT, instead of 1 part by weight of DEPT in the adhesive composition (P-1 part) of Example 1. Using this P-2 part, M-1 part, and M-2 part, the aforementioned tensile bond strength test (Q1) was conducted to determine the tensile bond strength. Further, for the multi-part type dental nonaqueous curable composition, the flexural strength test (Q2) was conducted to determine the flexural strength. Table 1 shows the results.

Dental Aqueous Adhesive Composition (P-2):

| MDP | 10 parts by weight |
|---|---|
| HEMA | 25 parts by weight |
| Water | 65 parts by weight |
| DEPT | 0.2 part by weight |

Example 3

P-3 part having the following composition was prepared using 8 parts by weight of DEPT instead of 1 part by weight of DEPT in the adhesive composition (P-1 part) of Example 1. Using this P-3 part, M-1 part, and M-2 part, the aforementioned tensile bond strength test (Q1) was conducted to determine the tensile bond strength. Further, for the multi-part type dental nonaqueous curable composition, the flexural strength test (Q2) was conducted to determine the flexural strength. Table 1 shows the results.

Dental Aqueous Adhesive Composition (P-3):

| MDP | 10 parts by weight |
|---|---|
| HEMA | 25 parts by weight |
| Water | 65 parts by weight |
| DEPT | 8 parts by weight |

Comparative Example 1

An adhesive composition (P-4) having the following composition in which DEPT was eliminated from P-1 part of the adhesive composition of Example 1 was prepared. Further, M-3 part having the following composition in which DEPT was eliminated from M-2 part of Example 1 was prepared. Sodium sulfite was dispersed in powder form in the composition obtained by mixing M-1 part and M-3 part. Using this P-4 part, M-1 part, and M-3 part, the aforementioned tensile bond strength test (Q1) and flexural strength test (Q2) were conducted to determine the tensile bond strength and the flexural strength, respectively. Table 1 shows the results.

Dental Aqueous Adhesive Composition (P-4):

| MDP | 10 parts by weight |
|---|---|
| HEMA | 25 parts by weight |
| Water | 65 parts by weight |

M-3 Part:

| Bis-GMA | 40 parts by weight |
|---|---|
| HEMA | 30 parts by weight |
| NPG | 30 parts by weight |

Sodium sulfite powder (average particle size: 6.1 μm) 1 part by weight

Example 4

A-1 part and B-1 part each having the following composition were prepared as a composite resin, instead of M-1 part and M-2 part of Example 1. Sodium sulfite was dispersed in powder form in the composition obtained by mixing A-1 part and B-1 part. Using this P-1 part, A-1 part, and B-1 part, the following tensile bond strength test (Q3) was conducted to determine the tensile bond strength. Further, for the multi-part type dental nonaqueous curable composition, the flexural strength test (Q2) was conducted to determine the flexural strength. Table 1 shows the results.

First Part (A-1 part):

| TEGDMA: | 35 parts by weight |
|---|---|
| GDEMA: | 10 parts by weight |
| Bis-GMA: | 30 parts by weight |
| D2.6E: | 25 parts by weight |
| BPO: | 1.5 parts by weight |

Silane-treated Ba glass: 288 parts by weight
Second Part (B-1 Part):

| | |
|---|---|
| TEGDMA: | 20 parts by weight |
| GDEMA: | 10 parts by weight |
| Bis-GMA: | 30 parts by weight |
| D2.6E: | 40 parts by weight |
| DEPT: | 1.5 parts by weight |

Sodium sulfite powder (average particle size: 6.1 μm): 1 part by weight
Silane-treated Ba glass: 288 parts by weight
R972: 3 parts by weight <<Tensile Bond Strength Test (Q3): Chemical Curing>>

The labial surface of a bovine mandibular incisor was ground with #80 silicon carbide paper (manufactured by NIHON KENSHI CO., LTD.) under running water to form a flat surface of dentin. The flat surface was further grounded with #1000 silicon carbide paper (manufactured by NIHON KENSHI CO., LTD.) under running water so as to be a smooth surface. An adhesive tape having a thickness of about 150 μm and being provided with a 4-mm-diameter circular hole was attached to the smooth surface, thereby defining the bonding area. Subsequently, the prepared dental aqueous adhesive composition P-1 was applied to the inside of the above-mentioned circular hole using a brush, which was left standing for 10 seconds. Thereafter, it was dried with an air syringe until the fluidity of the adhesive composition was lost. Next, a mixture of the first part (A-1 part) and the second part (B-1 part) of the prepared curable composition was mounted on the surface coated with the adhesive composition. After it was covered with a mold release film (product name "EVAL", manufactured by KURARAY CO., LTD.), a slide glass was mounted on and pressed against the mold release film, which was left standing for 30 minutes to be cured. Using a commercially available dental resin cement (product name "Panavia Fluoro Cement", manufactured by KURARAY MEDICAL INC.), one end of a 7 mm diameter×25 mm high cylindrical rod made of SUS304 was bonded to the obtained cured product, which was used as a specimen. 16 specimens were produced in total. After 1 hour from the bonding, the specimen was immersed in water at 37° C. After 24 hours, it was taken out from the water, and subjected to measurement of the tensile bond strength with a universal testing machine (manufactured by SHIMADZU CORPORATION). The measurement of the tensile bond strength was performed with a cross-head speed being set at 2 mm/min. The average of the measured values of 8 specimens was taken as the tensile bond strength.

The remaining 8 specimens bonded to dentin were further subjected to a thermal cycle load in which each specimen was immersed alternately in a water bath at 4° C. and a water bath at 60° C. each for 1 minute 4000 times, and thereafter the tensile bond strength was measured. The bond durability was evaluated from this tensile bond strength after the thermal cycle load. Table 1 shows the results.

TABLE 1

| | | | EX. 1 | C. EX. 1 | EX. 2 | EX. 3 | EX. 4 |
|---|---|---|---|---|---|---|---|
| Dental aqueous adhesive composition (A) | (a) Polymerizable monomer having an acidic group | MDP | 10 | 10 | 10 | 10 | 10 |
| | (b) Aliphatic polymerizable monomer having no acidic group | HEMA | 25 | 25 | 25 | 25 | 25 |
| | (e) Aromatic polymerizable monomer having no acidic group | Bis-GMA | | | | | |
| | (c) Water | | 65 | 65 | 65 | 65 | 65 |
| | (d1) Amine-based reducing agent | DEPT | 1 | — | 0.2 | 8 | 1 |
| Multi-part type dental nonaqueous curable composition (B) First part | (b) Aliphatic polymerizable monomer having no acidic group | TEGDMA | | | | | 35 |
| | | NPG | 30 | 30 | 30 | 30 | |
| | | GDEMA | | | | | 10 |
| | | HEMA | 30 | 30 | 30 | 30 | |
| | (e) Aromatic polymerizable monomer having no acidic group | Bis-GMA | 40 | 40 | 40 | 40 | 30 |
| | | D2.6E | | | | | 25 |
| | (g) Organic peroxide | BPO | 1 | 1 | 1 | 1 | 1.5 |
| | (i) Filler | Silane-treated Ba glass | | | | | 288 |
| Multi-part type dental nonaqueous curable composition (B) Second part | (b) Aliphatic polymerizable monomer having no acidic group | TEGDMA | | | | | 20 |
| | | NPG | 30 | 30 | 30 | 30 | |
| | | GDEMA | | | | | 10 |
| | | HEMA | 30 | 30 | 30 | 30 | |
| | (e) Aromatic polymerizable monomer having no acidic group | Bis-GMA | 40 | 40 | 40 | 40 | 30 |
| | | D2.6E | | | | | 40 |
| | (d2) Amine-based reducing agent | DEPT | 1.5 | — | 1.5 | 1.5 | 1.5 |
| | (f) Powdery water-soluble reducing compound | Sodium sulfite | 1 | 1 | 1 | 1 | 1 |
| | (i) Filler | Silane-treated Ba glass | | | | | 288 |
| | | R972 | | | | | 3 |
| Tensile bond strength to dentin/MPa | After placed in water at 37° C. for one day | | 13.5 | 14.6 | 11.7 | 10.8 | 13.7 |
| | After thermal cycle 4000 times | | 10.2 | 5.0 | 10.2 | 10.4 | 11.0 |
| Flexural strength/MPa | After placed in water at 37° C. for one day | | 62 | 63 | 64 | 63 | 120 |
| | After placed in water at 70° C. for one week (durability of flexural strength) | | 42 | 20 | 43 | 40 | 90 |
| Amine ratio (A)/(B) | | | 3.8 | — | 0.8 | 30.5 | 3.8 |

The following points can be seen from Table 1. The dental adhesive material kit of the present invention produced in each of Examples 1 to 4 has high bond strength to bovine dentin initially and after the thermal cycle, and exhibits excellent adhesiveness over a long period of time. On the other hand, the dental adhesive material kit produced in Comparative Example 1 has low bond strength to bovine dentin after the thermal cycle. Further, the multi-part type dental curable composition produced in each of Examples 1 to 4 maintains the flexural strength over a long period of time, and has excellent durability of flexural strength. On the other hand, the multi-part type dental curable composition produced in Comparative Example 1 has low durability of flexural strength.

Example 5

A dental aqueous adhesive composition (D-1 part) having the following composition was produced as a one-component dental adhesive agent. Further, using this D-1 part, and A-1 part and B-1 part of Example 4, the aforementioned tensile bond strength test (Q3) was conducted to determine the tensile bond strength. Further, for the multi-part type dental nonaqueous curable composition, the flexural strength test (Q2) was conducted to determine the flexural strength. Table 2 shows the results.

D-1 Part:

| | |
|---|---|
| MDP: | 10 parts by weight |
| HEMA: | 25 parts by weight |
| GDEMA: | 5 parts by weight |
| Bis-GMA: | 30 parts by weight |
| Water: | 15 parts by weight |
| Ethanol: | 15 parts by weight |
| DEPT: | 2 parts by weight |
| CQ: | 2 parts by weight |
| PDE: | 1 part by weight |
| BAPO: | 1 part by weight |
| R972: | 5 parts by weight |

Example 6

A dental adhesive agent (D-2 part) containing 10 parts by weight of 4-META, instead of 10 parts by weight of MDP, and 5 parts by weight of GDMA, instead of 5 parts by weight of GDEMA, in the dental adhesive agent (D-1 part) of Example 5 was prepared. Tests were conducted in the same manner as in Example 5 except that D-2 part was used as the dental adhesive agent. Table 2 shows the results.

Example 7

A dental adhesive agent (D-3 part) containing 10 parts by weight of MAC-10, instead of 10 parts by weight of MDP, and 5 parts by weight of NPG, instead of 5 parts by weight of GDEMA, in the dental adhesive agent (D-1 part) of Example 5 was prepared. Tests were conducted in the same manner as in Example 5 except that D-3 part was used as the dental adhesive agent. Table 2 shows the results.

Example 8

A dental adhesive agent (D-4 part) containing 10 parts by weight of 4-MET, instead of 10 parts by weight of MDP, in the dental adhesive agent (D-1 part) of Example 5 was prepared. Tests were conducted in the same manner as in Example 5 except that D-4 part was used as the dental adhesive agent. Table 2 shows the results.

Example 9

A dental adhesive agent (D-5 part) containing 10 parts by weight of PM, instead of 10 parts by weight of MDP, and 2 parts by weight of DMPT, instead of 2 parts by weight of DEPT, in the dental adhesive agent (D-1 part) of Example 5 was prepared. Tests were conducted in the same manner as in Example 5 except that D-5 part was used as the dental adhesive agent. Table 2 shows the results.

Example 10

A dental adhesive agent (D-6 part) was prepared by changing, in the dental adhesive agent (D-1 part) of Example 5, the content of MDP from 10 parts by weight to 15 parts by weight, the content of HEMA from 25 parts by weight to 30 parts by weight, the content of GDEMA from 5 parts by weight to 10 parts by weight, and the content of Bis-GMA from 30 parts by weight to 15 parts by weight. Tests were conducted in the same manner as in Example 5 except that D-6 part was used as the dental adhesive agent. Table 2 shows the results.

Example 11

A dental adhesive agent (D-7 part) was prepared by changing, in the dental adhesive agent (D-1 part) of Example 5, the content of MDP from 10 parts by weight to 20 parts by weight, the content of HEMA from 25 parts by weight to 10 parts by weight, the content of GDEMA from 5 parts by weight to 0 part by weight, and the content of Bis-GMA from 30 parts by weight to 40 parts by weight. Tests were conducted in the same manner as in Example 5 except that D-7 part was used as the dental adhesive agent. Table 2 shows the results.

Example 12

A dental adhesive agent (D-8 part) was prepared by changing, in the dental adhesive agent (D-1 part) of Example 5, the content of CQ from 2 parts by weight to 4 parts by weight, the content of PDE from 1 part by weight to 2 parts by weight, and the content of BAPO from 1 part by weight to 3 parts by weight. Tests were conducted in the same manner as in Example 5 except that D-8 part was used as the dental adhesive agent. Table 2 shows the results.

Example 13

A dental adhesive agent (D-9 part) was prepared by changing, in the dental adhesive agent (D-1 part) of Example 5, the content of CQ from 2 parts by weight to 0 part by weight, and the content of PDE from 1 part by weight to 0 part by weight. Tests were conducted in the same manner as in Example 5 except that D-9 part was used as the dental adhesive agent. Table 2 shows the results.

Example 14

A dental adhesive agent (D-10 part) was prepared by changing, in the dental adhesive agent (D-1 part) of Example 5, the content of MDP from 10 parts by weight to 5 parts by weight, the content of HEMA from 25 parts by weight to 10 parts by weight, the content of GDEMA from 5 parts by weight to 0 part by weight, the content of Bis-GMA from 30 parts by weight to 15 parts by weight, the content of water from 15 parts by weight to 45 parts by weight, and the content of ethanol from 15 parts by weight to 25 parts by weight. Tests were conducted in the same manner as in Example 5 except that D-10 part was used as the dental adhesive agent. Table 2 shows the results.

Example 15

A dental adhesive agent (D-11 part) was prepared by changing, in the dental adhesive agent (D-1 part) of Example 5, the content of HEMA from 25 parts by weight to 20 parts by weight, the content of GDEMA from 5 parts by weight to 0 part by weight, the content of water from 15 parts by weight to 5 parts by weight, and the content of ethanol from 15 parts by weight to 35 parts by weight. Tests were conducted in the same manner as in Example 5 except that D-11 part was used as the dental adhesive agent. Table 2 shows the results.

Example 16

A dental adhesive agent (D-12 part) was prepared by changing the content of R972 (filler) from 5 parts by weight to 1 part by weight in the dental adhesive agent (D-1 part) of Example 5. Tests were conducted in the same manner as in Example 5 except that D-12 part was used as the dental adhesive agent. Table 2 shows the results.

Example 17

A dental adhesive agent (D-13 part) was prepared by changing the content of R972 (filler) from 5 parts by weight to 8 parts by weight in the dental adhesive agent (D-1 part) of Example 5. Tests were conducted in the same manner as in Example 5 except that D-13 part was used as the dental adhesive agent. Table 2 shows the results.

Comparative Example 2

A dental adhesive agent (D-14 part) was prepared by changing the content of DEPT from 2 parts by weight to 0 part by weight in the dental aqueous adhesive agent (D-1 part) of Example 5. Further, (B-2 part) was prepared by changing the content of DEPT from 1.5 parts by weight to 0 part by weight in (B-1 part) of Example 4. Tests were conducted in the same manner as in Example 5 except that (D-14 part) as the dental adhesive agent and (B-2 part) was used instead of (D-1 part) and (B-1 part), respectively. Table 2 shows the results.

TABLE 2

| | | | EX. 5 | EX. 6 | EX. 7 | EX. 8 | EX. 9 | C. EX. 2 | EX. 10 | EX. 11 | EX. 12 | EX. 13 | EX. 14 | EX. 15 | EX. 16 | EX. 17 |
|---|---|---|---|---|---|---|---|---|---|---|---|---|---|---|---|---|
| Dental aqueous adhesive composition (A) | (a) Polymerizable monomer having an acidic group | MDP | 10 | | | | | 10 | 15 | 20 | 10 | 10 | 5 | 10 | 10 | 10 |
| | | 4-META | | 10 | | | | | | | | | | | | |
| | | MAC-10 | | | 10 | | | | | | | | | | | |
| | | 4-MET | | | | 10 | | | | | | | | | | |
| | | PM | | | | | 10 | | | | | | | | | |
| | (b) Aliphatic polymerizable monomer having no acidic group | HEMA | 25 | 25 | 25 | 25 | 25 | 25 | 30 | 10 | 25 | 25 | 10 | 20 | 25 | 25 |
| | | GDMA | | 5 | | | | | | | | | | | | |
| | | GDEMA | 5 | | | 5 | 5 | 5 | 10 | | 5 | 5 | | | 5 | 5 |
| | | NPG | | | 5 | | | | | | | | | | | |
| | (e) Aromatic polymerizable monomer having no acidic group | Bis-GMA | 30 | 30 | 30 | 30 | 30 | 30 | 15 | 40 | 30 | 30 | 15 | 30 | 30 | 30 |
| | (c) Water | | 15 | 15 | 15 | 15 | 15 | 15 | 15 | 15 | 15 | 15 | 45 | 5 | 15 | 15 |
| | (d1) Amine-based reducing agent | DEPT | 2 | 2 | 2 | 2 | | | 2 | 2 | 2 | 2 | 2 | 2 | 2 | 2 |
| | | DMPT | | | | | 2 | | | | | | | | | |
| | (h) Photopolymerization initiator | CQ/PDE | 2/1 | 2/1 | 2/1 | 2/1 | 2/1 | 2/1 | 2/1 | 2/1 | 4/2 | | 2/1 | 2/1 | 2/1 | 2/1 |
| | | BAPO | 1 | 1 | 1 | 1 | 1 | 1 | 1 | 1 | 3 | 1 | 1 | 1 | 1 | 1 |
| | Organic solvent | Ethanol | 15 | 15 | 15 | 15 | 15 | 15 | 15 | 15 | 15 | 15 | 25 | 35 | 15 | 15 |
| | (i) Filler | R972 | 5 | 5 | 5 | 5 | 5 | 5 | 5 | 5 | 5 | 5 | 5 | 5 | 1 | 8 |
| Multi-part type dental nonaqueous curable composition (B) First part | (b) Aliphatic polymerizable monomer having no acidic group | TEGDMA | 35 | 35 | 35 | 35 | 35 | 35 | 35 | 35 | 35 | 35 | 35 | 35 | 35 | 35 |
| | | GDEMA | 10 | 10 | 10 | 10 | 10 | 10 | 10 | 10 | 10 | 10 | 10 | 10 | 10 | 10 |
| | (e) Aromatic polymerizable monomer having no acidic group | Bis-GMA | 30 | 30 | 30 | 30 | 30 | 30 | 30 | 30 | 30 | 30 | 30 | 30 | 30 | 30 |
| | | D2.6E | 25 | 25 | 25 | 25 | 25 | 25 | 25 | 25 | 25 | 25 | 25 | 25 | 25 | 25 |
| | (g) Organic peroxide | BPO | 1.5 | 1.5 | 1.5 | 1.5 | 1.5 | 1.5 | 1.5 | 1.5 | 1.5 | 1.5 | 1.5 | 1.5 | 1.5 | 1.5 |
| | (i) Filler | Silane-treated Ba glass | 288 | 288 | 288 | 288 | 288 | 288 | 288 | 288 | 288 | 288 | 288 | 288 | 288 | 288 |
| Multi-part type dental nonaqueous curable composition (B) Second part | (b) Polymerizable monomer having no acidic group | TEGDMA | 20 | 20 | 20 | 20 | 20 | 20 | 20 | 20 | 20 | 20 | 20 | 20 | 20 | 20 |
| | | GDEMA | 10 | 10 | 10 | 10 | 10 | 10 | 10 | 10 | 10 | 10 | 10 | 10 | 10 | 10 |
| | (e) Aromatic polymerizable monomer having no acidic group | Bis-GMA | 30 | 30 | 30 | 30 | 30 | 30 | 30 | 30 | 30 | 30 | 30 | 30 | 30 | 30 |
| | | D2.6E | 40 | 40 | 40 | 40 | 40 | 40 | 40 | 40 | 40 | 40 | 40 | 40 | 40 | 40 |
| | (d2) Amine-based reducing agent | DEPT | 1.5 | 1.5 | 1.5 | 1.5 | 1.5 | | 1.5 | 1.5 | 1.5 | 1.5 | 1.5 | 1.5 | 1.5 | 1.5 |
| | (f) Powdery water-soluble reducing compound | Sodium sulfite | 1 | 1 | 1 | 1 | 1 | 1 | 1 | 1 | 1 | 1 | 1 | 1 | 1 | 1 |

TABLE 2-continued

|  |  |  | EX. 5 | EX. 6 | EX. 7 | EX. 8 | EX. 9 | C. EX. 2 | EX. 10 | EX. 11 | EX. 12 | EX. 13 | EX. 14 | EX. 15 | EX. 16 | EX. 17 |
|---|---|---|---|---|---|---|---|---|---|---|---|---|---|---|---|---|
|  | (i) Filler | Silane-treated Ba glass | 288 | 288 | 288 | 288 | 288 | 288 | 288 | 288 | 288 | 288 | 288 | 288 | 288 | 288 |
|  |  | R972 | 3 | 3 | 3 | 3 | 3 | 3 | 3 | 3 | 3 | 3 | 3 | 3 | 3 | 3 |
| Tensile bond strength to dentin/ MPa | After placed in water at 37° C. for one day | | 18.8 | 16.2 | 16.4 | 16.8 | 15.9 | 0 | 16.2 | 15.7 | 17.9 | 15.7 | 15.8 | 15.3 | 18.4 | 18.3 |
|  | After thermal cycle 4000 times | | 16.5 | 12.3 | 12.7 | 11.9 | 10.9 | 0 | 14.8 | 14.7 | 15.2 | 14.2 | 14.6 | 13.9 | 16.2 | 15.9 |
| Flexural strength/ MPa | After placed in water at 37° C. for one day | | 121 | 123 | 122 | 125 | 124 | 60 | 120 | 119 | 120 | 120 | 125 | 124 | 121 | 123 |
|  | After placed in water at 70° C. for one week (durability of flexural strength) | | 120 | 119 | 123 | 118 | 119 | 20 | 120 | 115 | 114 | 110 | 120 | 122 | 119 | 120 |
| Amine ratio (A)/(B) | | | 3.8 | 3.8 | 3.8 | 3.8 | 3.8 | — | 3.8 | 3.8 | 3.8 | 3.8 | 3.8 | 3.8 | 3.8 | 3.8 |

The following points can be seen from Table 2. The dental adhesive material kit containing the one-component dental adhesive agent of the present invention produced in each of Examples 5 to 17 has high bond strength to bovine dentin initially and after the thermal cycle, and exhibits excellent adhesiveness over a long period of time. On the other hand, the dental adhesive material kit produced in Comparative Example 2 cannot adhere to bovine dentin. Further, the multi-part type dental curable composition produced in each of Examples 5 to 17 maintains the flexural strength over a long period of time, and has excellent durability of flexural strength. On the other hand, the multi-part type dental curable composition produced in Comparative Example 2 has low durability of flexural strength.

Example 18

A dental adhesive agent (D-15 part) was prepared by changing the content of DEPT from 2 parts by weight to 0.5 part by weight in the dental adhesive agent (D-1 part) of Example 5. Further, a second part (B-3 part) was prepared by changing the content of DEPT from 1.5 parts by weight to 1 part by weight in B-1 part. Tests were conducted in the same manner as in Example 5 except that D-15 part was used as the dental adhesive agent and B-3 part was used as the second part of the dental curable composition. Table 3 shows the results.

Example 19

A second part (B-4 part) was prepared by changing the content of DEPT from 1 part by weight to 2 parts by weight in the second part (B-3 part) of Example 18. Tests were conducted in the same manner as in Example 18 except that B-4 part was used as the second part of the dental curable composition. Table 3 shows the results.

Example 20

A dental adhesive agent (D-16 part) was prepared by changing the content of DEPT from 2 parts by weight to 1.5 parts by weight in the dental adhesive agent (D-1 part) of Example 5. Tests were conducted in the same manner as in Example 18 except that D-16 part was used as the dental adhesive agent. Table 3 shows the results.

Example 21

Tests were conducted in the same manner as in Example 20 except that the second part (B-4 part) of Example 19 was used instead of the second part (B-3 part) of Example 20. Table 3 shows the results.

Example 22

A second part (B-5 part) was prepared by changing the content of DEPT from 1 part by weight to 4 parts by weight in the second part (B-3 part) of Example 20. Tests were conducted in the same manner as in Example 20 except that B-5 part was used as the second part of the dental curable composition. Table 3 shows the results.

Example 23

A dental adhesive agent (D-17 part) was prepared by changing the content of DEPT from 2 parts by weight to 8 parts by weight in the dental adhesive agent (D-1 part) of Example 5. Tests were conducted in the same manner as in Example 5 except that D-17 part was used as the dental adhesive agent and B-3 part of Example 18 was used as the second part of the dental curable composition. Table 3 shows the results.

Example 24

A first part (A-2 part) was prepared by changing, in the first part (A-1 part) of Example 18, the content of TEGDMA from 35 parts by weight to 15 parts by weight, the content of GDEMA from 10 parts by weight to 5 parts by weight, the content of Bis-GMA from 30 parts by weight to 45 parts by weight, and the content of D2.6E from 25 parts by weight to 35 parts by weight. Further, a second part (B-6 part) was prepared by changing, in the second part (B-3 part), the content of TEGDMA from 20 parts by weight to 15 parts by weight, the content of GDEMA from 10 parts by weight to 5 parts by weight, the content of Bis-GMA from 30 parts by weight to 45 parts by weight, and the content of D2.6E from 40 parts by weight to 35 parts by weight. Tests were conducted in the same manner as in Example 18 except that A-2 part was used as the first part of the dental curable composition, and B-6 part was used as the second part thereof. Table 3 shows the results.

Example 25

A first part (A-3 part) was prepared by changing, in the first part (A-1 part) of Example 18, the content of TEGDMA from 35 parts by weight to 40 parts by weight, the content of GDEMA from 10 parts by weight to 5 parts by weight, the content of Bis-GMA from 30 parts by weight to 10 parts by weight, and the content of D2.6E from 25 parts by weight to 10 parts by weight. Further, a second part (B-7 part) was prepared by changing, in the second part (B-3 part), the content of TEGDMA from 20 parts by weight to 40 parts by weight, the content of GDEMA from 10 parts by weight to 5 parts by weight, the content of Bis-GMA from 30 parts by weight to 10 parts by weight, and the content of D2.6E from 40 parts by weight to 10 parts by weight. Tests were conducted in the same manner as in Example 18 except that A-3 part was used as the first part of the dental curable composition, and B-7 part was used as the second part thereof. Table 3 shows the results.

Example 26

A first part (A-4 part) was prepared by changing the content of BPO from 1.5 parts by weight to 0.5 part by weight in the first part (A-1 part) of Example 18. Tests were conducted in the same manner as in Example 18 except that A-4 part was used as the first part of the dental curable composition. Table 3 shows the results.

Example 27

A first part (A-5 part) was prepared by changing the content of BPO from 1.5 parts by weight to 5 parts by weight in the first part (A-1 part) of Example 18. Tests were conducted in the same manner as in Example 18 except that A-5 part was used as the first part of the dental curable composition. Table 3 shows the results.

Example 28

A first part (A-6 part) was prepared by changing the content of silane-treated Ba glass from 288 parts by weight to 100 parts by weight in the first part (A-1 part) of Example 18. Further, a second part (B-8 part) was prepared by changing the content of silane-treated Ba glass from 288 parts by weight to 100 parts by weight in the second part (B-3 part). Tests were conducted in the same manner as in Example 18 except that A-6 part was used as the first part of the dental curable composition, and B-8 part was used as the second part thereof. Table 3 shows the results.

Example 29

A first part (A-7 part) was prepared by changing the content of silane-treated Ba glass from 288 parts by weight to 500 parts by weight in the first part (A-1 part) of Example 18. Further, a second part (B-9 part) was prepared by changing the content of silane-treated Ba glass from 288 parts by weight to 500 parts by weight in the second part (B-3 part). Tests were conducted in the same manner as in Example 18 except that A-7 part was used as the first part of the dental curable composition, and B-9 part was used as the second part thereof. Table 3 shows the results.

TABLE 3

| | | | EX. 18 | EX. 19 | EX. 20 | EX. 21 | EX. 22 | EX. 23 | EX. 24 | EX. 25 | EX. 26 | EX. 27 | EX. 28 | EX. 29 |
|---|---|---|---|---|---|---|---|---|---|---|---|---|---|---|
| Dental aqueous adhesive composition (A) | (a) Polymerizable monomer having an acidic group | MDP | 10 | 10 | 10 | 10 | 10 | 10 | 10 | 10 | 10 | 10 | 10 | 10 |
| | (b) Aliphatic polymerizable monomer having no acidic group | HEMA | 25 | 25 | 25 | 25 | 25 | 25 | 25 | 25 | 25 | 25 | 25 | 25 |
| | | GDEMA | 5 | 5 | 5 | 5 | 5 | 5 | 5 | 5 | 5 | 5 | 5 | 5 |
| | (e) Aromatic polymerizable monomer having no acidic group | Bis-GMA | 30 | 30 | 30 | 30 | 30 | 30 | 30 | 30 | 30 | 30 | 30 | 30 |
| | (c) Water | | 15 | 15 | 15 | 15 | 15 | 15 | 15 | 15 | 15 | 15 | 15 | 15 |
| | (d1) Amine-based reducing agent | DEPT | 0.5 | 0.5 | 1.5 | 1.5 | 1.5 | 8 | 0.5 | 0.5 | 0.5 | 0.5 | 0.5 | 0.5 |
| | (h) Photopolymerization initiator | CQ/PDE | 2/1 | 2/1 | 2/1 | 2/1 | 2/1 | 2/1 | 2/1 | 2/1 | 2/1 | 2/1 | 2/1 | 2/1 |
| | | BAPO | 1 | 1 | 1 | 1 | 1 | 1 | 1 | 1 | 1 | 1 | 1 | 1 |
| | Organic solvent | Ethanol | 15 | 15 | 15 | 15 | 15 | 15 | 15 | 15 | 15 | 15 | 15 | 15 |
| | (i) Filler | R972 | 5 | 5 | 5 | 5 | 5 | 5 | 5 | 5 | 5 | 5 | 5 | 5 |
| Multi-part type dental nonaqueous curable composition (B) First part | (b) Polymerizable monomer having no acidic group and no aromatic ring | TEGDMA | 35 | 35 | 35 | 35 | 35 | 35 | 15 | 40 | 35 | 35 | 35 | 35 |
| | | GDEMA | 10 | 10 | 10 | 10 | 10 | 10 | 5 | 5 | 10 | 10 | 10 | 10 |
| | (e) Aromatic polymerizable monomer having no acidic group | Bis-GMA | 30 | 30 | 30 | 30 | 30 | 30 | 45 | 10 | 30 | 30 | 30 | 30 |
| | | D2.6E | 25 | 25 | 25 | 25 | 25 | 25 | 35 | 10 | 25 | 25 | 25 | 25 |
| | (g) Organic peroxide | BPO | 1.5 | 1.5 | 1.5 | 1.5 | 1.5 | 1.5 | 1.5 | 1.5 | 0.5 | 5 | 1.5 | 1.5 |
| | (i) Filler | Silane-treated Ba glass | 288 | 288 | 288 | 288 | 288 | 288 | 288 | 288 | 288 | 288 | 100 | 500 |
| Multi-part type dental nonaqueous curable composition (B) Second part | (b) Aliphatic polymerizable monomer having no acidic group | TEGDMA | 20 | 20 | 20 | 20 | 20 | 20 | 15 | 40 | 20 | 20 | 20 | 20 |
| | | GDEMA | 10 | 10 | 10 | 10 | 10 | 10 | 5 | 5 | 10 | 10 | 10 | 10 |
| | (e) Aromatic polymerizable monomer having no acidic group | Bis-GMA | 30 | 30 | 30 | 30 | 30 | 30 | 45 | 10 | 30 | 30 | 30 | 30 |
| | | D2.6E | 40 | 40 | 40 | 40 | 40 | 40 | 35 | 10 | 40 | 40 | 40 | 40 |
| | (d2) Amine-based reducing agent | DEPT | 1 | 2 | 1 | 2 | 4 | 1 | 1 | 1 | 1 | 1 | 1 | 1 |

TABLE 3-continued

|  |  |  | EX. 18 | EX. 19 | EX. 20 | EX. 21 | EX. 22 | EX. 23 | EX. 24 | EX. 25 | EX. 26 | EX. 27 | EX. 28 | EX. 29 |
|---|---|---|---|---|---|---|---|---|---|---|---|---|---|---|
|  | (f) Powdery water-soluble reducing compound | Sodium sulfite | 1 | 1 | 1 | 1 | 1 | 1 | 1 | 1 | 1 | 1 | 1 | 1 |
|  | (i) Filler | Silane-treated Ba glass | 288 | 288 | 288 | 288 | 288 | 288 | 288 | 288 | 288 | 288 | 100 | 500 |
|  |  | R972 | 3 | 3 | 3 | 3 | 3 | 3 | 3 | 3 | 3 | 3 | 3 | 3 |
| Tensile bond strength to dentin/ MPa | After placed in water at 37° C. for one day | | 18.9 | 18.8 | 17.6 | 16.8 | 16.2 | 15.7 | 17.8 | 15.1 | 18.7 | 17.9 | 15.3 | 18.8 |
| | After thermal cycle 4000 times | | 15.5 | 14.9 | 16.9 | 15.8 | 12.3 | 11.9 | 16.3 | 13.9 | 15.3 | 16.1 | 15.1 | 16.6 |
| Flexural strength/ MPa | After placed in water at 37° C. for one day | | 122 | 123 | 120 | 120 | 119 | 120 | 140 | 118 | 118 | 123 | 110 | 150 |
| | After placed in water at 70° C. for one week (durability of flexural strength) | | 118 | 119 | 120 | 117 | 118 | 124 | 145 | 120 | 115 | 127 | 115 | 145 |
| Amine ratio (A)/(B) | | | 1.4 | 0.7 | 4.3 | 2.1 | 1.1 | 22.9 | 1.4 | 1.4 | 1.4 | 1.4 | 1.4 | 1.4 |

The following points can be seen from Table 3. The dental adhesive material kit containing the one-component dental adhesive agent of the present invention produced in each of Examples 18 to 29 has high bond strength to bovine dentin initially and after the thermal cycle, and exhibits excellent adhesiveness over a long period of time. Further, the multi-part type dental curable composition produced in each of Examples 18 to 29 maintains the flexural strength over a long period of time, and has excellent durability of flexural strength.

Example 30

B-10 part was prepared by changing the content of sodium sulfite powder from 1 part by weight to 0.1 part by weight in the second part (B-1 part) of the dental curable composition of Example 5. Tests were conducted in the same manner as in Example 5 except that B-10 part was used as the second part of the dental curable composition. Table 4 shows the results.

Example 31

B-11 part was prepared by changing the content of sodium sulfite powder from 1 part by weight to 3 parts by weight in the second part (B-1 part) of the dental curable composition of Example 5. Tests were conducted in the same manner as in Example 30 except that B-11 part was used as the second part of the dental curable composition. Table 4 shows the results.

Comparative Example 3

B-12 part was prepared by changing the content of sodium sulfite powder from 1 part by weight to 0 part by weight in the second part (B-1 part) of the dental curable composition of Example 5. Tests were conducted in the same manner as in Example 30 except that B-12 part was used as the second part of the dental curable composition. Table 4 shows the results.

TABLE 4

|  |  |  | EX. 30 | EX. 31 | C. EX. 3 |
|---|---|---|---|---|---|
| Dental aqueous adhesive composition (A) | (a) Polymerizable monomer having an acidic group | MDP | 10 | 10 | 10 |
| | (b) Aliphatic polymerizable monomer having no acidic group | HEMA | 25 | 25 | 25 |
| | | GDEMA | 5 | 5 | 5 |
| | (e) Aromatic polymerizable monomer having no acidic group | Bis-GMA | 30 | 30 | 30 |
| | (c) Water | | 15 | 15 | 15 |
| | (d1) Amine-based reducing agent | DEPT | 2 | 2 | 2 |
| | (h) Photopolymerization initiator | CQ/PDE | 2/1 | 2/1 | 2/1 |
| | | BAPO | 1 | 1 | 1 |
| | Organic solvent | Ethanol | 15 | 15 | 15 |
| | (i) Filler | R972 | 5 | 5 | 5 |
| Multi-part type dental nonaqueous curable composition (B) First part | (b) Polymerizable monomer having no acidic group and no aromatic ring | TEGDMA | 35 | 35 | 35 |
| | | GDEMA | 10 | 10 | 10 |
| | (e) Aromatic polymerizable monomer having no acidic group | Bis-GMA | 30 | 30 | 30 |
| | | D2.6E | 25 | 25 | 25 |
| | (g) Organic peroxide | BPO | 1.5 | 1.5 | 1.5 |
| | (i) Filler | Silane-treated Ba glass | 288 | 288 | 288 |
| | | R972 | | | |
| Multi-part type dental nonaqueous curable composition (B) Second part | (b) Aliphatic polymerizable monomer having no acidic group | TEGDMA | 20 | 20 | 20 |
| | | GDEMA | 10 | 10 | 10 |
| | (e) Aromatic polymerizable monomer having no acidic group | Bis-GMA | 30 | 30 | 30 |
| | | D2.6E | 40 | 40 | 40 |
| | (d2) Amine-based reducing agent | DEPT | 1.5 | 1.5 | 1.5 |
| | (f) Powdery water-soluble reducing compound | Sodium sulfite | 0.1 | 3 | 0 |
| | (i) Filler | Silane-treated Ba glass | 288 | 288 | 288 |
| | | R972 | 3 | 3 | 3 |

TABLE 4-continued

| | | EX. 30 | EX. 31 | C. EX. 3 |
|---|---|---|---|---|
| Tensile bond strength to dentin/MPa | After placed in water at 37° C. for one day | 12.2 | 17.8 | 1.0 |
| | After thermal cycle 4000 times | 10.2 | 15.4 | 0.3 |
| Flexural strength/MPa | After placed in water at 37° C. for one day | 123 | 110 | 121 |
| | After placed in water at 70° C. for one week (durability of flexural strength) | 120 | 95 | 120 |
| Amine ratio (A)/(B) | | 3.8 | 3.8 | 3.8 |

The following points can be seen from Table 4. The dental adhesive material kit containing the one-component dental adhesive agent of the present invention produced in each of Examples 16 and 17 has high bond strength to bovine dentin initially and after the thermal cycle, and exhibits excellent adhesiveness over a long period of time. On the other hand, the dental adhesive material kit produced in Comparative Example 3 has low bond strength to bovine dentin after the thermal cycle. Further, the multi-part type dental curable composition produced in each of Examples 30 and 31 maintains the flexural strength over a long period of time, and has excellent durability of flexural strength.

Example 32

A-8 part was prepared by adding 1.5 parts by weight of CQ and 0.2 part by weight of BAPO to the first part (A-1 part) of the dental curable composition of Example 4. Further, B-13 part was prepared by adding 2 parts by weight of PDE to the second part (B-1 part) of the dental curable composition of Example 4. Using D-1 part, and these A-8 part and B-13 part, the following tensile bond strength test (Q4) and flexural strength test (Q5) were conducted to determine the bond strength and the flexural strength, respectively. Table 5 shows the results.

<<Tensile Bond Strength Test (Q4): Photocuring>>

The labial surface of a bovine mandibular incisor was ground with #80 silicon carbide paper (manufactured by NIHON KENSHI CO., LTD.) under running water to form a flat surface of dentin. The flat surface was further grounded with #1000 silicon carbide paper (manufactured by NIHON KENSHI CO., LTD.) under running water so as to be a smooth surface. An adhesive tape having a thickness of about 150 μm and being provided with a 4-mm-diameter circular hole was attached to the smooth surface, thereby defining the bonding area. Subsequently, the prepared dental aqueous adhesive composition D-1 was applied to the inside of the above-mentioned circular hole using a brush, which was left standing for 10 seconds. Thereafter, it was dried with an air syringe until the fluidity of the adhesive composition was lost. Next, a mixture of the first part and the second part of the prepared curable composition was mounted on the surface coated with the adhesive composition. After it was covered with a mold release film (product name "EVAL", manufactured by KURARAY CO., LTD.), a slide glass was mounted on and pressed against the mold release film. The pressed surface was irradiated with light for 10 seconds, using a dental visible light unit (JET LITE 3000, manufactured by Morita Corporation), to be cured. Using a commercially available dental resin cement (product name "Panavia Fluoro Cement", manufactured by KURARAY MEDICAL INC.), one end of a 7 mm diameter×25 mm high cylindrical rod made of SUS304 was bonded to the obtained cured product, which was used as a specimen. 16 specimens were produced in total. After 1 hour from the bonding, the specimen was immersed in water at 37° C. After 24 hours, it was taken out from the water, and subjected to measurement of the tensile bond strength with a universal testing machine (manufactured by SHIMADZU CORPORATION). The measurement of the tensile bond strength was performed with a cross-head speed being set at 2 mm/min. The average of the measured values of 8 specimens was taken as the tensile bond strength.

The remaining 8 specimens bonded to dentin were further subjected to a thermal cycle load in which each specimen was immersed alternately in a water bath at 4° C. and a water bath at 60° C. each for 1 minute 4000 times, and thereafter the tensile bond strength was measured. The bond durability was evaluated from this tensile bond strength after the thermal cycle load.

<<Bending Test (Q5): Strength of Photocured Product>>

Equal amounts of the first part and the second part of the prepared multi-part type dental nonaqueous curable composition were collected, and mixed for 30 seconds. The obtained mixture was charged into a stainless steel mold (size: 2 mm×2 mm×25 mm), and thereafter it was pressed from above and below each with a slide glass, and both sides thereof were irradiated with light at 5 points on each side for 20 seconds per point, using a dental visible light unit (JET LITE 3000, manufactured by Morita Corporation), to be cured. The cured product was separated from the mold, which was used as a specimen. 10 specimens were produced and deburred. The cured product was placed in water at 37° C. for 24 hours. Thereafter, the flexural strength of the cured product was measured, using a universal testing machine (product code "AGI-100", manufactured by SHIMADZU CORPORATION), with the span being set at 20 mm and a cross-head speed being set at 1 mm/min. The average of the measured values of 5 specimens was taken as the flexural strength. The remaining 5 specimens were further placed in water at 70° C. for one week, and thereafter subjected to measurement of the flexural strength. This was taken as the durability of flexural strength.

Example 33

A-9 part was prepared by changing, in the first part (A-8 part) of the dental curable composition of Example 32, the content of CQ to 0.1 part by weight and the content of BAPO to 0.5 part by weight. Further, B-14 part was prepared by changing the content of PDE to 0.2 part by weight in the second part (B-13 part) of the dental curable composition of Example 32. Using D-1 part, and these A-9 part and B-14 part, the tensile bond strength and the flexural strength were determined in the same manner as in Example 32. Table 5 shows the results.

TABLE 5

| | | | EX. 32 | EX. 33 |
|---|---|---|---|---|
| Dental aqueous adhesive composition (A) | (a) Polymerizable monomer having an acidic group | MDP | 10 | 10 |
| | (b) Aliphatic polymerizable monomer having no acidic group | HEMA | 25 | 25 |
| | | GDEMA | 5 | 5 |
| | (e) Aromatic polymerizable monomer having no acidic group | Bis-GMA | 30 | 30 |
| | (c) Water | | 15 | 15 |
| | (d1) Amine-based reducing agent | DEPT | 2 | 2 |
| | (h) Photopolymerization initiator | CQ/PDE | 2/1 | 2/1 |
| | | BAPO | 1 | 1 |
| | Organic solvent | Ethanol | 15 | 15 |
| | (i) Filler | R972 | 5 | 5 |
| Multi-part type dental nonaqueous curable composition (B) First part | (b) Polymerizable monomer having no acidic group and no aromatic ring | TEGDMA | 35 | 35 |
| | | GDEMA | 10 | 10 |
| | (e) Aromatic polymerizable monomer having no acidic group | Bis-GMA | 30 | 30 |
| | | D2.6E | 25 | 25 |
| | (g) Organic peroxide | BPO | 1.5 | 1.5 |
| | (h) Photopolymerization initiator | CQ | 1.5 | 0.1 |
| | | BAPO | 0.2 | 0.5 |
| | (i) Filler | Silane-treated Ba glass | 288 | 288 |
| Multi-part type dental nonaqueous curable composition (B) Second part | (b) Aliphatic polymerizable monomer having no acidic group | TEGDMA | 20 | 20 |
| | | GDEMA | 10 | 10 |
| | (e) Aromatic polymerizable monomer having no acidic group | Bis-GMA | 30 | 30 |
| | | D2.6E | 40 | 40 |
| | (d2) Amine-based reducing agent | DEPT | 1.5 | 1.5 |
| | (f) Powdery water-soluble reducing compound | Sodium sulfite | 1 | 1 |
| | (h) Photopolymerization initiator | PDE | 2 | 0.2 |
| | (i) Filler | Silane-treated Ba glass | 288 | 288 |
| | | R972 | 3 | 3 |
| Tensile bond strength to dentin/MPa | After placed in water at 37° C. for one day | | 18.9 | 18.2 |
| | After thermal cycle 4000 times | | 17.1 | 16.9 |
| Flexural strength/MPa (Photocuring) | After placed in water at 37° C. for one day | | 147 | 140 |
| | After placed in water at 70° C. for one week (durability of flexural strength) | | 142 | 137 |

The following points can be seen from Table 5. The dental adhesive material kit containing the one-component dental adhesive agent of the present invention produced in each of Examples 32 and 33 has high bond strength to bovine dentin initially and after the thermal cycle, and exhibits excellent adhesiveness over a long period of time. Further, the multi-part type dental curable composition produced in each of Examples 32 and 33 maintains the flexural strength over a long period of time, and has excellent durability of flexural strength.

INDUSTRIAL APPLICABILITY

The dental adhesive material kit of the present invention is used suitably when forming an abutment in the field of dental care.

The invention claimed is:

1. A dental adhesive material kit comprising:
a dental aqueous adhesive composition (A); and
a multi-part type dental nonaqueous curable composition (B), wherein
the dental aqueous adhesive composition (A) contains a polymerizable monomer (a) having an acidic group, an aliphatic polymerizable monomer (b) having no acidic group, water (c), and an amine-based reducing agent (d1) containing no sulfur atom, and
the multi-part type dental nonaqueous curable composition (B) contains an aliphatic polymerizable monomer (b) having no acidic group, an aromatic polymerizable monomer (e) having no acidic group, a powdery water-soluble reducing compound (f) containing a sulfur atom, an organic peroxide (g), and an amine-based reducing agent (d2) containing no sulfur atom.

2. The dental adhesive material kit according to claim 1, wherein
a content of the polymerizable monomer (a) having an acidic group is 1 to 40 parts by weight, a content of the aliphatic polymerizable monomer (b) having no acidic group is 10 to 50 parts by weight, and a content of the water (c) is 5 to 75 parts by weight, in 100 parts by weight of the total amount of polymerizable monomers and solvents contained in the dental aqueous adhesive composition (A), and a content of the amine-based reducing agent (d1) is 0.1 to 10 parts by weight, with respect to 100 parts by weight of the total amount of polymerizable monomers in the dental aqueous adhesive composition (A), and
a content of the aliphatic polymerizable monomer (b) having no acidic group is 20 to 75 parts by weight, and a content of the aromatic polymerizable monomer (e) having no acidic group is 25 to 80 parts by weight, in 100 parts by weight of the total amount of polymerizable monomers in the multi-part type dental nonaqueous curable composition (B), and a content of the powdery water-soluble reducing compound (f) is 0.1 to 3 parts by weight, a content of the organic peroxide (g) is 0.1 to 10 parts by weight, and a content of the amine-based reducing agent (d2) is 0.25 to 4 parts by weight, with respect to 100 parts by weight of the total amount of polymerizable monomers in the multi-part type dental nonaqueous curable composition (B).

3. The dental adhesive material kit according to claim 2, wherein
a ratio (d1/d2) of the weight of the amine-based reducing agent (d1), when the total amount of polymerizable monomers contained in the dental aqueous adhesive composition (A) is taken as 100 parts by weight, and the weight of the amine-based reducing agent (d2), when the total amount of polymerizable monomers contained in the dental nonaqueous curable composition (B) is taken as 100 parts by weight, is 0.5/1 to 35/1.

4. The dental adhesive material kit according to claim 1, wherein
the dental aqueous adhesive composition (A) further contains an aromatic polymerizable monomer (e) having no acidic group.

5. The dental adhesive material kit according to claim 1, wherein
the dental aqueous adhesive composition (A) further contains a photopolymerization initiator (h).

6. The dental adhesive material kit according to claim 1, wherein
the dental aqueous adhesive composition (A) further contains a filler (i).

7. The dental adhesive material kit according to claim 1, wherein
the dental nonaqueous curable composition (B) further contains a filler (i).

8. The dental adhesive material kit according to claim 1, wherein
the amine-based reducing agents (d1) and (d2) each are an aromatic amine having no electron-withdrawing group on its aromatic ring.

9. The dental adhesive material kit according to claim 1, wherein
the powdery water-soluble reducing compound (f) is sulfite or bisulfate in powder form.

10. The dental adhesive material kit according to claim 1, wherein
the dental aqueous adhesive composition (A) is a one-component dental adhesive agent.

11. The dental adhesive material kit according to claim 1, being a dental material kit for core construction.

* * * * *